(12) United States Patent
Grawunder et al.

(10) Patent No.: US 12,121,527 B2
(45) Date of Patent: *Oct. 22, 2024

(54) ANTHRACYCLINE-BASED ANTIBODY DRUG CONJUGATES HAVING HIGH IN VIVO TOLERABILITY

(71) Applicant: NBE-Therapeutics AG, Basel (CH)

(72) Inventors: Ulf Grawunder, Hersberg (CH); Roger Beerli, Aldikon bei Regensdorf (CH); Remy Gebleux, Basel (CH)

(73) Assignee: NBE-THERAPEUTICS AG, Basel (CH)

( * ) Notice: Subject to any disclaimer, the term of this patent is extended or adjusted under 35 U.S.C. 154(b) by 664 days.

This patent is subject to a terminal disclaimer.

(21) Appl. No.: 16/925,802

(22) Filed: Jul. 10, 2020

(65) Prior Publication Data

US 2021/0023103 A1 Jan. 28, 2021

Related U.S. Application Data

(63) Continuation of application No. 16/533,429, filed on Aug. 6, 2019, now Pat. No. 10,758,556, which is a continuation of application No. PCT/EP2018/071389, filed on Aug. 7, 2018.

(30) Foreign Application Priority Data

Aug. 7, 2017 (EP) .................................. 17185107

(51) Int. Cl.
| | |
|---|---|
| *A61K 31/704* | (2006.01) |
| *A61K 47/68* | (2017.01) |
| *A61P 35/00* | (2006.01) |
| *C07K 16/30* | (2006.01) |

(52) U.S. Cl.
CPC ........ *A61K 31/704* (2013.01); *A61K 47/6801* (2017.08); *A61P 35/00* (2018.01); *C07K 16/30* (2013.01)

(58) Field of Classification Search
CPC ............ A61K 47/6855; A61K 47/6849; A61K 47/6801; A61K 47/6889; A61K 47/6809; A61K 31/704; A61K 47/65; A61K 2039/505; A61P 35/00; C07K 16/00; C07K 16/30; C07K 16/2803; C07K 16/32; C07K 2317/55
See application file for complete search history.

(56) References Cited

U.S. PATENT DOCUMENTS

| | | | |
|---|---|---|---|
| 7,462,608 B2 | 12/2008 | Chen et al. | |
| 8,212,009 B2 | 7/2012 | Kipps et al. | |
| 8,703,801 B2 | 4/2014 | Nair et al. | |
| 9,150,647 B2 | 10/2015 | Mellstedt et al. | |
| 9,163,258 B2 | 10/2015 | Riddell et al. | |
| 9,228,023 B2 | 1/2016 | Rohlff et al. | |
| 9,242,014 B2 | 1/2016 | Kipps et al. | |
| 9,266,952 B2 | 2/2016 | Teige | |
| 9,316,646 B2 | 4/2016 | Rader et al. | |
| 9,758,586 B2 | 9/2017 | Rader et al. | |
| 9,872,923 B2 * | 1/2018 | Grawunder | ............. A61P 31/00 |
| 9,933,434 B2 | 4/2018 | Kipps et al. | |
| 9,938,350 B2 | 4/2018 | Kipps | |
| 10,041,090 B2 | 8/2018 | Gao et al. | |
| 10,188,745 B2 * | 1/2019 | Grawunder | ........ A61K 47/6867 |
| 10,517,959 B2 | 12/2019 | Grawunder et al. | |
| 10,618,959 B2 * | 4/2020 | Rader | .................. C07K 14/705 |
| 10,758,556 B2 * | 9/2020 | Grawunder | ............. C07K 16/30 |
| 10,864,277 B2 * | 12/2020 | Grawunder | ............. A61K 47/65 |
| 10,960,083 B2 * | 3/2021 | Grawunder | ...... C12Y 304/2207 |
| 11,364,301 B2 * | 6/2022 | Grawunder | ............. A61P 31/00 |
| 2003/0113762 A1 | 6/2003 | Warrington | |
| 2008/0318212 A1 | 12/2008 | Wilson et al. | |
| 2011/0008347 A1 | 1/2011 | Ullrich et al. | |
| 2012/0058051 A1 | 3/2012 | Rader et al. | |
| 2012/0219506 A1 | 8/2012 | Moore et al. | |
| 2012/0282177 A1 | 11/2012 | Rohlff et al. | |
| 2013/0131139 A1 | 5/2013 | Tyner et al. | |
| 2013/0251723 A1 | 9/2013 | Rohlff et al. | |
| 2013/0273073 A1 | 10/2013 | Kipps et al. | |
| 2013/0281922 A1 | 10/2013 | Teige | |
| 2014/0004156 A1 | 1/2014 | Mellstedt et al. | |
| 2015/0258143 A1 | 9/2015 | Malarkannan | |
| 2015/0306141 A1 | 10/2015 | Jensen et al. | |
| 2016/0002335 A1 | 1/2016 | Williams et al. | |
| 2016/0122430 A1 | 5/2016 | Gish et al. | |
| 2016/0297881 A1 | 10/2016 | Vu et al. | |
| 2016/0362472 A1 | 12/2016 | Bitter et al. | |

(Continued)

FOREIGN PATENT DOCUMENTS

| | | | |
|---|---|---|---|
| EP | 3219731 A1 | 9/2017 | |
| JP | 6817492 | 12/2020 | |

(Continued)

OTHER PUBLICATIONS

Milani A et al. Role of trastuzumab in the management of HER2-positive metastatic breast cancer. Breast Cancer: Targets and Therapy 2010:2 93-109. (Year: 2010).*

Strop P et al. Location Matters: Site of Conjugation Modulates Stability and Pharmacokinetics of Antibody Drug Conjugates. (Chem and Bio 2013 20(2) 161-167). (Year: 2013).*

(Continued)

*Primary Examiner* — Karen A. Canella
*Assistant Examiner* — John J Skoko, III
(74) *Attorney, Agent, or Firm* — Morgan, Lewis & Bockius LLP

(57) ABSTRACT

The present invention relates to antibody drug conjugates (ADCs) presenting improved properties of in vivo tolerability.

19 Claims, 9 Drawing Sheets

Specification includes a Sequence Listing.

(56) References Cited

U.S. PATENT DOCUMENTS

| | | |
|---|---|---|
| 2017/0015746 A1 | 1/2017 | Jensen |
| 2017/0029774 A1 | 2/2017 | Jensen |
| 2017/0051252 A1 | 2/2017 | Morgan et al. |
| 2017/0152297 A1 | 6/2017 | Jensen |
| 2017/0198045 A1 | 7/2017 | Johnson et al. |
| 2017/0204176 A1 | 7/2017 | Bonvini et al. |
| 2017/0210799 A1 | 7/2017 | Anderson et al. |
| 2017/0226183 A1 | 8/2017 | Schiffer-Mannioui |
| 2017/0233472 A1 | 8/2017 | Barat et al. |
| 2017/0246279 A1 | 8/2017 | Berger et al. |
| 2017/0267742 A1 | 9/2017 | Jensen et al. |
| 2017/0275374 A1 | 9/2017 | Schiffer-Mannioui |
| 2017/0283497 A1 | 10/2017 | Schiffer-Mannioui |
| 2017/0306018 A1 | 10/2017 | Vu et al. |
| 2017/0306044 A1 | 10/2017 | Vu et al. |
| 2017/0335281 A1 | 11/2017 | Loew et al. |
| 2017/0363630 A1 | 12/2017 | Petricoin et al. |
| 2018/0009891 A1 | 1/2018 | Jensen |
| 2018/0066063 A1 | 3/2018 | Kipps et al. |
| 2018/0112002 A1 | 4/2018 | Kipps et al. |
| 2018/0127503 A1 | 5/2018 | Liu et al. |
| 2018/0142016 A1 | 5/2018 | Wong et al. |
| 2018/0147271 A1 | 5/2018 | Morgan et al. |
| 2018/0340026 A1 | 11/2018 | Rader et al. |
| 2019/0040132 A1 | 2/2019 | Balakrishnan et al. |
| 2019/0153092 A1 | 5/2019 | Waldmeier et al. |
| 2021/0139579 A1 | 5/2021 | Grawunder et al. |

FOREIGN PATENT DOCUMENTS

| | | |
|---|---|---|
| WO | WO2003016484 A2 | 2/2003 |
| WO | WO2003042397 A2 | 5/2003 |
| WO | WO2003091264 A2 | 11/2003 |
| WO | WO2005100605 A1 | 10/2005 |
| WO | 2005102387 A2 | 11/2005 |
| WO | WO2007051077 A2 | 5/2007 |
| WO | WO2007146957 A2 | 12/2007 |
| WO | WO2008066498 A1 | 6/2008 |
| WO | WO2008076868 A2 | 6/2008 |
| WO | WO2008103849 A2 | 8/2008 |
| WO | WO2009099741 A1 | 8/2009 |
| WO | WO2010016634 A2 | 2/2010 |
| WO | WO2010124188 A1 | 10/2010 |
| WO | WO2011054007 A1 | 5/2011 |
| WO | WO2011057034 A2 | 5/2011 |
| WO | WO2011071849 A2 | 6/2011 |
| WO | WO2011159847 A2 | 12/2011 |
| WO | WO2012012695 A2 | 1/2012 |
| WO | WO2012045085 A1 | 4/2012 |
| WO | WO2012073217 A1 | 6/2012 |
| WO | WO2012075158 A1 | 6/2012 |
| WO | WO2012076066 A1 | 6/2012 |
| WO | WO2012076727 A1 | 6/2012 |
| WO | WO2012097313 A2 | 7/2012 |
| WO | WO2014013026 A1 | 1/2014 |
| WO | WO2014031174 A1 | 2/2014 |
| WO | WO2014031687 A1 | 2/2014 |
| WO | WO2014055413 A2 | 4/2014 |
| WO | WO2014140317 A2 | 9/2014 |
| WO | WO2014167022 A1 | 10/2014 |
| WO | WO2015113110 A1 | 8/2015 |
| WO | WO2015142675 A2 | 9/2015 |
| WO | WO2015157384 A1 | 10/2015 |
| WO | WO2015157386 A1 | 10/2015 |
| WO | WO2015157391 A1 | 10/2015 |
| WO | WO2015157399 A1 | 10/2015 |
| WO | WO2015157432 A1 | 10/2015 |
| WO | WO2015164745 A1 | 10/2015 |
| WO | WO2015184203 A1 | 12/2015 |
| WO | WO2015184207 A1 | 12/2015 |
| WO | WO2016016343 A1 | 2/2016 |
| WO | WO2016016344 A1 | 2/2016 |
| WO | WO2016034666 A1 | 3/2016 |
| WO | WO2016055592 A1 | 4/2016 |
| WO | WO2016055593 A1 | 4/2016 |
| WO | WO2016069647 A1 | 5/2016 |
| WO | 2016102679 | 6/2016 |
| WO | WO2016094373 A1 | 6/2016 |
| WO | WO2016094873 A2 | 6/2016 |
| WO | WO-2016102679 A1 * | 6/2016 | ............ A61K 47/64 |
| WO | 2016127081 A1 | 8/2016 |
| WO | WO2016142768 A1 | 9/2016 |
| WO | WO2016150564 A2 | 9/2016 |
| WO | WO2016164731 A2 | 10/2016 |
| WO | WO2016172726 A1 | 10/2016 |
| WO | WO2016187216 A1 | 11/2016 |
| WO | WO2016187220 A2 | 11/2016 |
| WO | WO2017053469 A2 | 3/2017 |
| WO | 2017072361 | 5/2017 |
| WO | WO2017072361 A1 | 5/2017 |
| WO | WO2017107541 A1 | 6/2017 |
| WO | 2017127664 | 7/2017 |
| WO | WO2017127499 A1 | 7/2017 |
| WO | WO2017127664 A1 | 7/2017 |
| WO | WO2017136607 A1 | 8/2017 |
| WO | WO2017142928 A1 | 8/2017 |
| WO | 2019030223 | 2/2019 |

OTHER PUBLICATIONS

Papayannopoulos IA Characterising therapeutic antibodies and ADCs using mass spectrometry. European Pharmaceutical Review 2016 issue 4 www.europeanpharmaceuticalreview.com/article/43622/therapeutic-antibodies-mass-spectrometry (Year: 2016).*

U.S. Department of Health and Human Services Food and Drug Administration Center for Drug Evaluation and Research (CDER) Pharamcology and Toxicology, 2005, 1-27 (Year: 2005).*

Office Action from corresponding Indian Patent Application No. 202027004154 dated Jun. 11, 2021 (7 pages).

Office Action for corresponding Korean patent application No. 10-2020-7005294 dated Sep. 28, 2021.

Office Action for corresponding European application No. 18758828.0 dated Dec. 15, 2021.

Office Action for corresponding Japanese application No. 2020-214394 dated Mar. 1, 2022.

Office Action for corresponding Korean patent application No. 10-2020-7005294 dated Apr. 1, 2022.

Balakrishnan et al., "Analysis of ROR1 Protein Expression in Human Cancer and Normal Tissues", Clinical Cancer Research 23:3061-3071, Nov. 16, 2016, doi: 10.1158/1078-0432).

Baskar et al., "Targeting malignant B cells with an immunotoxin against ROR1", mAbs. (2012), 4:3, 349-361.

Baskar et al., "Unique Cell Surface Expression of Receptor Tyrosine Kinase ROR1 in Human B-Cell Chronic Lymphocytic Leukemia" Clin Cancer Res. (2008), 14(2):396-404.

Beerli et al., "Sortase Enzyme-Mediated Generation of Site-Specifically Conjugated Antibody Drug Conjugates with high In Vitro and In Vivo Potency"; PloS One 10, e131177, Jul. 1, 2015.

Behrens et al. (2014) "Methods for site-specific drug conjugation to antibodies," MABS, vol. 6, No. 1, pp. 46-53.

Berger et al., "Safety of Targeting ROR1 in Primates with Chimeric Antigen Receptor-Modified T Cells", Cancer Immunol. Res. 3(2):2016-216 doi: 10.1158/2326-6066.CIR-14-0163, Feb. 2015.

Chen et al., "A general strategy for the evolution of bond-forming enzymes using yeast display"; PNAS, 108(28), 2011.

Choi et al., "Pre-clinical Specificity and Safety of UC-961, a First-In-Class Monoclonal Antibody Targeting ROR1", Clinical Lymphoma Myeloma and Leukemia 15:S167-9, 2015.

Cui et al. "High-level ROR1 associates with accelerated disease progression in chronic lymphocytic leukemia", Blood 128(25), p. 2931-2940 Dec. 22, 2016.

Daneshmanesh et al., "Monoclonal antibodies against ROR1 induce apoptosis of chronic lymphocytic leukemia (CLL) cells", Leukemia. (2012), 26:1348-1355.

Daneshmanesh et al., "ROR1, a cell surface receptor tyrosine kinase is expressed in chronic lymphocytic", Int. J. Cancer (2008), 123: 1190-1195.

Dorr et al., "Reprogramming the specificity of sortase enzymes", PNAS, 2014.

(56) References Cited

OTHER PUBLICATIONS

Dorywalska et al., "Site-Dependent Degradation of a Non-Cleavable Auristatin-Based Linker-Payload in Rodent Plasma and its Effect on ADC Efficacy"; PLOS ONE, 2015.
Drake et al., "Aldehyde Tag Coupled with HIPS Chemistry Enables the Production of ADCs Conjugated Site-specifically to Different Antibody Regions with Distinct In vivo Efficacy and PK Outcomes"; Bioconjugate Chemistry, 25, 2014.
Fukuda et al., "Antisera induced by infusions of autologous ad-CD154-leukemia B cells identify ROR1 as an oncofetal antigen and receptor for Wnt5a", PNAS. (2008), 105(8):3047-3052.
Grawunder, "Development of best-in-class, homogeneous Antibody Drug conjugates (ADCs) for highly effective and safer cancer therapy", NBE-Therapeutics AG, Feb. 2016, 25 pages.
Hudecek et al., "The B-cell tumor-associated antigen ROR1 can be targeted with T cells modified to express a ROR1-specific chimeric antigen receptor", Blood (2010), DOI 10.1182/blood-2010-05-283309.
International Search Report in related PCT Application No. PCT/US2017014311 mailed Mar. 30, 2017 (6 pages).
International Search Report of PCT/EP2016/058156 mailed Oct. 20, 2016, 4 pp.
International Search Report with Written Opinion corresponding to International Patent Application No. PCT/EP2016/076244, mailed Mar. 27, 2017.
Jain et al., "Current ADC Linker Chemistry"; Pharma Res, 32, 2015.
Johnson et al., "Relationships between drug activity in NCI preclinical in vitro and in vivo models and early clinical trials", British Journal of Cancer, 2001, vol. 84, No. 10, pp. 1424-1431.
MacKeigan et al., "Sensitized RNAi screen of human kinases and phosphatases identifies new regulators of apoptosis and chemoresistance", Nat Cell Biol. (2005), DOI: 10.1038/ncb1258:1-10.
Masiakowski et al., "A Novel Family of Cell Surface Receptors with Tyrosine Kinase-like Domain", J Biol Chem. (1992), 267(36):26181-26190.
Patterson et al., "Improving the Serum Stability of Site-Specific Antibody Conjugates with Sulfone Linkers", Bioconjugate Chemistry 25:1402-1407, 2014.
Peng et al., "Mining Naïve Rabbit Antibody Repertoires by Phage Display for Monoclonal Antibodies of Therapeutic Utility", J Mol Biol. 429(19): 2954-2973, doi:10.1016/j.jmb.2017.08.003 2017.
Quintieri et al. (2005) "Metabolite of Nemorubicin in Human Liver Microsomes Formation and Antitumor Activity of PNU-159682, A Major Updated version," Clin. Cancer Res., vol. 11, pp. 1608-1617.
Quintieri et al., "Formation and Antitumor Activity of PNU-159682, A Major Metabolite of Nemorubicin in Human Liver Microsomes"; Clin Cancer Res, 11, 2005.
Rebagay et al., "ROR1 and ROR2 in human malignancies: potentials for targeted therapy", Frontiers in Oncology 2(34), doi:10.3389/fonc.2012.00034 Apr. 18, 2012.
Sausville et al., "Contributions of Human Tumor Xenografts to Anticancer Drug Development", Cancer Research, Apr. 2006, vol. 66, Issue 7, pp. 3351-3354.
Shabani et al., "Receptor tyrosine kinase-like orphan receptor 1: a novel target for cancer immunotherapy", Expert Opin. Ther. Targets 19(7), 2015.
Spirig et al., "Sortase enzymes in Gram-positive bacteria"; Molecular Microbiology, 82(5), 2011.
Stefan et al. (2017) "Highly Potent, Anthracycline-based Antibody-Drug Conjugates Generated by Enzymatic, Site-specific Conjugation," Molecular Cancer Therapeutics, vol. 16, No. 5, pp. 879-892.
Strop et al., "Location Matters: Site of Conjugation Modulates Stability and Pharmacokinetics of Antibody Drug Conjugates"; Chemistry & Biology, 20, 2013.
Swindells, et al., "abYsis: Integrated Antibody Sequence and Structure-Management, Analysis, and Prediction"; J. Mol. Biol. 429, 356-364, 2017.
Tyner et al., "RNAi screen for rapid therapeutic target identification in leukemia patients", PNAS (2009), 106(21):8695-8700.
Waldmeier et al., "Transpo-mAb display: Transposition-mediated B cell display and functional screening of full-length IgG antibody libraries"; mAbs, 8(4), 2016.
Australian Office Action in corresponding Australian Patent Application No. 2018315127, dated Jan. 6, 2021, 5 pages.
Canadian Office Action in corresponding Canadian Patent Application No. 3,071,212, dated Mar. 5, 2021, 5 pages.
Canadian Office Action in corresponding Canadian Patent Application No. 3,071,212, dated Aug. 11, 2022, 3 pages.
Korean Office Action in corresponding Korean Patent Application No. 10-2020-7005294, dated Sep. 28, 2021, 11 pages.
Israeli Office Action in corresponding Israeli Patent Application No. 272534, dated Nov. 16, 2020, 10 pages.
European Office Action in corresponding application No. 118758828, dated Dec. 15, 2021, 6 pages.
Office Action in corresponding Japanese Patent Application No. 2020-214394, dated Mar. 1, 2022, 2 pages.
Office Action in corresponding Japanese Patent Application No. 2020-506746, dated Jul. 6, 2020, 11 pages.
Korean Office Action in corresponding Korean Patent Application No. 10-2020-7005294, dated Jun. 1, 2022, 3 pages.
Russian Office Action in corresponding Russian Patent Application No. 2020103344, dated Mar. 24, 2020, 3 pages.
English translation of Russian Office Action in corresponding Russian Patent Application No. 2020103344, dated Dec. 10, 2020, 8 pages.
English translation of Russian Office Action in corresponding Russian Patent Application No. 2020103344, dated Jul. 27, 2020, 9 pages.
Russian Prior Art Search, 2 pages.
Office Action in corresponding U.S. Appl. No. 16/533,429, dated Dec. 9, 2019, Grawunder et al., 13 pages.
International Preliminary Report on Patentability in corresponding WO2019030223, dated Feb. 11, 2020, 11 pages.
International Search Report in corresponding WO2019030223, dated Jan. 9, 2019, 7 pages.
Written Opinion in corresponding WO2019030223, dated Jan. 9, 2019, 10 pages.
Office Action from corresponding Russian Patent Application No. 2020103344/04 dated Jun. 1, 2021 (11 pages).
Drake et al., "Aldehyde Tag Coupled with HIPS Chemistry Enables the Production of ADCs Conjuttated Site-specifically to Different Antibody Ret1ions with Distinct In vivo Efficacy and PK Outcomes"; Bioconjugate Chemistry, 25, 2014.
Hudecek et al., "Receptor Affinity and Extracellular Domain Modifications Affect Tumor Recognition by ROR1-Specific Chimeric Antigen Receptor T Cells", Clin Cancer Res; 19(12), Apr. 25, 2013, 13 pages.
Jain et al., "Current ADC Linker Ct1ernistry"; Pharma Res, 32, 20i 5.
Peng et al., "Mining Nafve Rabbit Antibody Repertoires by Phage Display for Monoclonal Antibodies of Therapeutic Utility", J Mol Biol. 429(19): 2954-2973, doi: 10.1016/j.jmb.2017 .08.003 2017.
Ulf Grawunder, "Development of best-in-class, homogeneous Antibody Drug conjugates (ADCs) for highly effective and safer cancer therapy", NBE-Therapeutics AG, Feb. 2016, 25 pages.
Sausville et al. (Cancer Research, 2006, vol. 66, pp. 3351-3354) (Year: 2006).
Johnson et al. (British J. of Cancer, 2001, 84(10): 1424-1431) (Year: 2001).
Office Action for Canadian Patent Application No. 3,071,212, mailed Sep. 7, 2021 (4 pages).
New Zealand Patent Examination Report 1 dated Apr. 4, 2023, issued in foreign counterpart Application No. 761287 (4 pages).
Office Action for Chinese Patent Application No. 201880061886.7, mailed Sep. 21, 2023, 4 pages.
Office Action for corresponding Israeli Patent Application No. 272534 dated Sep. 28, 2023.
Office Action for corresponding Chinese Patent Application No. 201880061886.7 dated Feb. 28, 2023.
Office Action for corresponding Brazilian Patent Application No. BR112020002368-0 dated Nov. 30, 2023.

(56) References Cited

OTHER PUBLICATIONS

Radhakrishnan S. et al. "Elotuzumab as a novel anti-myeloma immunotherapy", Hum. Vaccin. Immunother. Aug. 3, 2017, vol. 13, No. 8, pp. 1751-1757.
Office Action (with partial translation) for corresponding Mexican Patent Application No. Mx/a/2020/001212 dated Mar. 22, 2024, 12 pages.
International Search Report in corresponding PCT/EP2018/071389, dated Jan. 9, 2019, 7 pages.

\* cited by examiner

Ab LC C-terminus —— linker comprising a peptidic sequence —— Anthracycline molecule

Fig. 1

ANTHRACYCLINE-BASED ANTIBODY DRUG CONJUGATES HAVING HIGH IN VIVO TOLERABILITY

RELATED APPLICATIONS

This application is a continuation of U.S. patent application Ser. No. 16/533,429, filed Aug. 6, 2019, which is a continuation of International Patent Application No. PCT/EP2018/071389, filed Aug. 7, 2018, which claims the benefit of European Patent Application No. 17185107.4, filed Aug. 7, 2017, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 10, 2020, is named 707915_NBE9-010PCCON2_ST25.txt and is 43,681 bytes in size.

FIELD OF THE INVENTION

The present invention relates to antibody drug conjugates carrying potent drugs and presenting improved properties in vivo and particularly improved tolerability in vivo.

BACKGROUND

Covalent conjugates of small molecular weight toxins (toxic "small molecules", MW<2'500 Daltons) to binding proteins, in particular to antibodies specific for tumor cells, are powerful tools to specifically target cancer cells for their destruction. Such antibody drug conjugates (ADCs) are of high medical and commercial interest for the therapy of cancer. In order to develop effective and safe ADCs for cancer therapy, several aspects need to be addressed: first, the antibody needs to be specific for a given tumor specific antigen (TSA), which should hardly or ideally not be expressed by normal or healthy tissue cells. Second, the covalent bond, or linkage, between the drug and the antibody/binding protein needs to be stable enough in circulation to prevent undesired release of the toxic payload in the blood stream while also effectively releasing the drug upon binding to and/or internalization into cancer cells. Third, the ADC has to be internalized in substantive quantities. Fourth, the toxic payload has to be released from the antibody and enter the appropriate cellular compartment to exert its toxicity. Fifth, the toxic payload has to be of high enough toxicity, or potency, in order to cause destruction of cancer cells, even if potentially limited amounts of the TSA are expressed on the cancer cells and therefore only limited amounts of the ADC are internalized, or if release of the toxic payload is not undertaken with high enough efficiency upon binding to the cancer cells, or upon internalization into the cancer cell.

However, equally, ADC's must also avoid inducement of side effects, generally mediated through (a) on-target binding in non-target tissues due to expression of the TSA on healthy cells, (b) off-target binding, due to binding of antigens besides the intended TSA, and/or (c) general toxicity, which may be caused by premature drug payload release in the bloodstream, released payload from lysed target cells or released metabolites.

These multiple constraints on ADC development make this type of therapeutic among the most challenging to bring through clinical evaluation. Moreover, because of the high costs of making and testing such biologic-based products, the skilled person is not at liberty to systematically test all possible variants and combinations of antibodies, linkers and toxins, as well as the particular conjugation site(s) and ratio of toxin to antibody.

Indeed, the literature reports on a multitude of possible toxin payloads and linkers (see for example Jain et al., 2015), and moreover, on a multitude of possible conjugation sites and conjugation methods.

In "Location Matters: Site of Conjugation Modulates Stability and Pharmacokinetics of Antibody Drug Conjugates" (Strop et al., Chemistry & Biology, 20, 2013), the authors report on ADCs conjugated by microbial transglutaminases. MMAD toxins conjugated to their antibody heavy and light chain C-termini presented similar efficacies both in vivo and in vitro. Doses of 10 and 25 mg/kg of ADC were equally well tolerated in rats.

The Applicant has surprisingly found that ADCs bearing anthracycline toxins bound at one or more specific sites, namely exclusively on the C-termini of one or both antibody (or antibody derivative) light chains, are not only therapeutically effective but, remarkably, are more highly tolerated in vivo than comparable ADCs with anthracycline toxins bound at alternative sites, i.e., on the C-termini of one or both antibody heavy chains or on a combination of the C-termini of the antibody heavy and light chains. Such a teaching is nowhere found in WO 2016/150564 (the contents of which are incorporated herein by reference), which refers to toxins in the same class but only to their attachment to a combination of the C-termini of the antibody heavy and light chains.

Teachings referring to means of toxin attachment of antibody C-termini, namely in WO 2014/140317 (the contents of which are incorporated herein by reference), also make no reference to preferential attachment of anthracycline toxins to the light-chain C-termini.

It is hence an object of the present invention to provide an antibody drug conjugate (ADC) that presents improved properties in vivo, and in particular is highly tolerated in vivo. In particular, it is an object of the present invention to provide an antibody drug conjugate that is better tolerated in vivo than its counterpart comprising the same number of the same toxins but attached to alternative C-termini.

It is another object of the present invention to provide a pharmaceutical composition comprising such an antibody drug conjugate.

It is another object of the present invention to provide a method of making such an antibody drug conjugate.

It is another object of the present invention to provide an antibody drug conjugate for use in the treatment of a subject that is suffering from, at risk of developing, and/or diagnosed with a neoplastic disease.

It is another object of the present invention to provide an antibody drug conjugate for use in the treatment of a subject that is suffering from, at risk of developing, and/or diagnosed with an immune disease or disorder.

These and further objects are met with methods and means according to the independent claims of the present invention. The dependent claims are related to specific embodiments.

SUMMARY OF THE INVENTION

The present invention provides antibody drug conjugates presenting improved properties in vivo including improved properties of in vivo tolerability. The invention and general advantages of its features will be discussed in detail below.

DESCRIPTION OF THE FIGURES

FIG. 1 depicts a general anthracycline-comprising ADC as per the invention, wherein Ab refers to an antibody or fragment or derivative joined at one or both of its constant region light chain C-termini to the linker comprising a peptidic sequence, leading to the anthracycline molecule toxin.

DEFINITIONS

Figure 2:
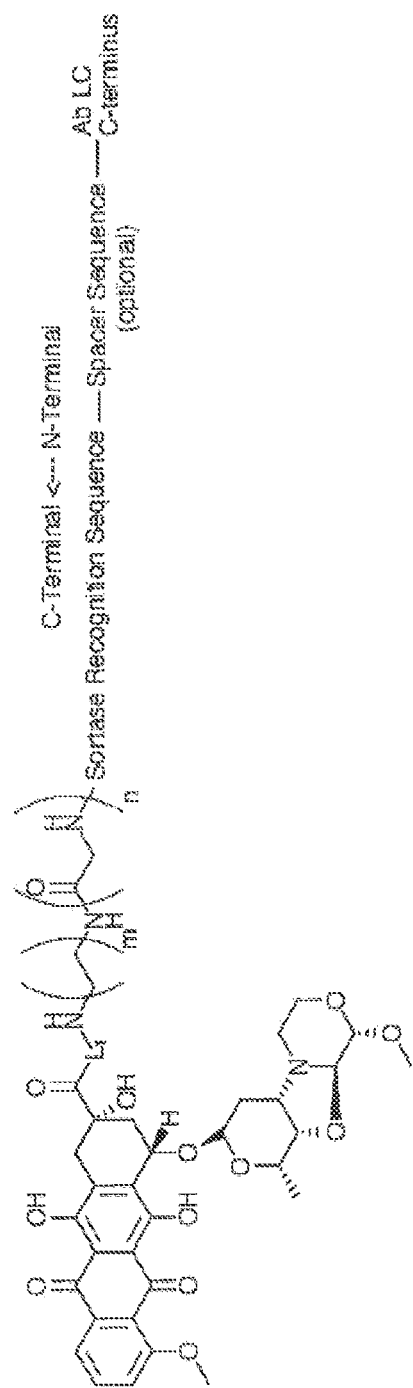
FIG. 2 depicts a preferred embodiment of the anthracycline molecule-comprising ADC as per the invention wherein:
the anthracycline molecule corresponds to a PNU derivative of formula (i)
$L_1$ is an optional linker, which may be a cleavable linker
m is greater than or equal to 1 and less than or equal to 11, and preferably m is 2
n is greater than or equal to 1 and less than or equal to 21, and preferably n is 1, 2, 3, 4 or 5
the Sortase Recognition Sequence here represents the product (e.g. LPXT) of specific cleavage of a sortase enzyme recognition motif (e.g. LPXTG) (depicted in C- to N-terminal orientation on the Figure), where X is any amino acid
the Spacer Sequence is optional (depicted in C- to N-terminal orientation on the Figure)
Ab is an antibody joined at one or both of its constant region light chain C-termini to the Spacer Sequence (if present), or to the Sortase Recognition Sequence (if the Spacer Sequence is absent).

Unless defined otherwise, all technical and scientific terms used herein have the same meaning as commonly understood by those of ordinary skill in the art to which this invention pertains. In addition, the following definitions are provided to assist the reader in the practice of the invention.

The term "antibody" refers to polypeptide chain(s) which exhibit a strong monovalent, bivalent or polyvalent binding to a given antigen, epitope or epitopes. Unless otherwise noted, antibodies can be generated using any suitable technology, e.g., hybridoma technology, ribosome display, phage display, gene shuffling libraries, semi-synthetic or fully synthetic libraries or combinations thereof. Antibodies of the invention are intact antibodies (e.g., IgG1 antibodies exemplified herein). Unless otherwise specified herein, all peptide sequences, including all antibody and antigen-binding fragment sequences are referred to in N→C order.

An intact antibody typically comprises at least two heavy (H) chains (about 45-70 kD) and two light (L) chains (about 20-25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Each heavy chain of an antibody is comprised of a heavy chain variable region ($V_H$) and a heavy chain constant region. In the case of IgG, the heavy chain constant region is comprised of three domains, $C_{H1}$, $C_{H2}$ and $C_{H3}$. Each light chain is comprised of a light chain variable region ($V_L$) and a light chain constant region. The light chain constant region is comprised of one domain, CL. The variable regions of the heavy and light chains contain a binding domain that interacts with an antigen. The constant regions of the antibodies mediate the binding of the immunoglobulin to host tissues or factors, including various cells of the immune system expressing Fc receptors and the first component (C1q) of the classical complement system. Monoclonal antibodies (mAbs) consist of identical (with respect to their encoded amino acid sequences) antibody molecules.

The $V_H$ and $V_L$ regions of an antibody can be further subdivided into regions of hypervariability, also termed complementarity-determining regions (CDRs), which are interspersed with the more conserved framework regions (FRs). Each VII and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined, e.g., the IMGT system and the Kabat system.

Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG.

Furthermore, the antibody can be contained in a derivative format ("antibody derivative") such as the dual variable domain immunoglobulin (DVD-Ig) format and single-chain variable fragment (scFv) fusions with IgA, IgD, IgE, IgG, or IgM. A single-chain variable region fragment (scFv) is a single-chain antibody, i.e., it is a polypeptide comprising a VII domain and a $V_L$ domain in polypeptide linkage, generally linked via a spacer peptide. scFv fusions be to the N- or C-terminus of the heavy chain, or to the N-terminus of the light chain. The DVD-Ig format consists of an Ig shaped antibody wherein each $V_L/V_H$ pair carries, N-terminally, another $V_L/V_H$ pair. The two $V_L/V_H$ pairs have the same or different antigen binding specificity. Also, the antibody can be present in a fragment of the typical antibody format, like F(ab), F(ab')2 or single chain FV (scFv). For the avoidance of doubt, both the terms antibody derivative and antibody fragment refer to embodiments that retain target binding capacity, i.e., exclude embodiments that are no longer capable of binding a target.

The terms "chimeric antibody" refer to antibody that contains antigen-binding regions (VII and $V_L$) targeting an antigen from one species, and a constant region corresponding to the immunoglobulin sequence of another species.

A "non-human antibody" refers to an antibody that does not contain a constant region corresponding to a human immunoglobulin sequence.

The terms "humanized antibody" refer to a chimeric antibody that contains sequences derived from human and non-human (e.g., rabbit) immunoglobulins such that some or all (for example, maintaining only the non-human CDR3 sequences of the light and heavy chains as in Rader C. et al., 1998), or substantially all of the CDR regions are of non-human origin, while substantially all of the FR regions correspond to those of a human immunoglobulin sequence.

The antibody or fragment or derivative described herein can be produced by enzymatic or chemical modification of the intact antibodies, or synthesized de novo using recombinant DNA methodologies, or identified using phage display libraries. Methods for generating these antibodies or antibody derivatives are well known in the art.

The antibody or fragment or derivative of the invention can be produced by any suitable technique, for example, using any suitable eukaryotic or non-eukaryotic expression or cell-free system. In certain embodiments, the antibody or fragment or derivative is produced using a mammalian expression system. In certain embodiments, the antibody or fragment or derivative is produced using an insect expression system.

"Therapeutically active compounds" refer, in the present invention, to compounds providing a therapeutically beneficial effect, and include, in particular, antibody drug conjugates. Therapeutically active compounds are often formulated as a composition, e.g., are formulated in a physiologically-acceptable buffer.

"Tolerability" refers to the degree to which adverse effects of an administered composition (comprising or consisting of a therapeutically active compound) can be tolerated by a human or other animal, e.g., by a mouse, rat, rabbit, monkey, etc., or by a group of humans or other animals. In one embodiment, tolerability can be determined relative to the rate of mortality.

"Adverse effects or events" are undesirable effects or events resulting from administration of a therapeutically active compound. In particular, adverse effects include weight loss, in particular weight loss in excess of 10%, 15%, or 20% of initial weight on day of treatment with a therapeutically active compound. In particular, adverse effects include death (in animal models, whether naturally occurring or following fulfillment of euthanasia criteria). In particular, adverse effects relating to deaths be assessed in animal models (e.g., groups of mice, rats, etc.) following a single or repeated (constant or escalating) dose of a therapeutically active compound as compared to an alternative therapeutically active compound and/or to a buffer control. In particular, tolerability be assessed in animal models in terms of a maximum tolerated dose, i.e., in terms of number of deaths within groups of animals treated with therapeutically active compound, wherein given groups treated with a given dose of compound over a dose range.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

DETAILED DESCRIPTION OF THE INVENTION

Before the invention is described in detail, it is to be understood that this invention is not limited to the particular component parts of the devices described or process steps of the methods described as such devices and methods vary. It is also to be understood that the terminology used herein is for purposes of describing particular embodiments only and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure and avoid lengthy repetitions.

Antibody Drug Conjugates (ADCs)

According to a first aspect, the invention refers to an antibody drug conjugate (ADC) comprising an antibody, or antibody fragment or derivative retaining target binding properties, comprising at least one light chain constant region C-terminus, and an anthracycline-based small molecule, wherein the anthracycline molecule(s) is/are exclusively linked to the light chain constant region C-terminus/i of the antibody, fragment or derivative, and wherein the anthracycline-based small molecule is linked, via a linker comprising a peptidic sequence, to said antibody, fragment or derivative.

The "anthracycline-based small molecule" is also called "anthracycline molecule" herein.

Relative to the ADC of the invention, is intended that no anthracycline molecules are covalently joined to the antibody at sites other than one or both of the antibody or fragment or derivative light chain constant region C-termini.

A visual depiction of the ADC according to the present invention is given in FIG. 1.

Aspects of the Invention Relating to the Antibody

The antibody of the invention can be of any isotype including, without limitation, IgA, IgD, IgE, IgG, or IgM. Thus, for example, the antibody can be any IgA such as IgA1 or IgA2, or any IgG such as IgG1, IgG2, IgG3, IgG4, or synthetic IgG.

Furthermore, the antibody can be contained in derivative formats ("antibody derivative") such as the dual variable domain immunoglobulin (DVD-Ig) format and single-chain variable fragment (scFv) fusions with IgA, IgD, IgE, IgG, or IgM. In a preferred embodiment, the antibody derivative is of DVD-Ig format.

The antibody or fragment or derivative be a monovalent, a bivalent or multi-valent antibody.

The antibody or fragment or derivative be mono- or multi-specific. The term "multi-specific" means an antibody or fragment or derivative that has specificity for two or more different epitopes of a given antigen, or that has specificity for at least two different antigens.

In a preferred embodiment, the antibody is an IgG antibody.

The antibody or fragment or derivative target (or bind to) any antigen, but preferentially targets an antigen that is tumor specific or that is expressed at a higher rate on tumor tissue than on healthy tissue.

As used herein, "expressed at a higher rate" means expressed at least 10% higher, preferably at least 20% higher, more preferably at least 30% higher, more preferably at least 40% higher, more preferably at least 50% higher, more preferably at least 60% higher, more preferably at least 70% higher, more preferably at least 80% higher, more preferably at least 90% higher, and even more preferably at least 100% higher. The expression rate can be determined with methods from the art known by the skilled person, like RT-PCR, or Immunohistochemistry.

In particular, the antigen be a human antigen. In a preferred embodiment, the antigen is ROR1, ROR2, CS1, mesothelin or HER2, and more preferably ROR1, CS1, or HER2, and even more preferably is ROR1 or HER2. In particular, the antigen may be human ROR1 (based on sequence NP_005003 from GenBank), human ROR2 (based on sequence NP_004551.2 from GenBank), human CS1 (based on sequence NM_021181.3 from GenBank), human mesothelin (based on sequence NP_037536 from GenBank) or human HER2 (based on sequence NP_004439 from GenBank). In one embodiment, the antibody or fragment or derivative does not bind to human and/or mouse CS1, and in this embodiment, preferably the antibody or fragment or derivative does not bind to human CS1.

In a preferred embodiment, the antibody or fragment or derivative comprises the CDRs of the antibodies or antibody derivatives presented in the Examples. In particular, the antibody or fragment or derivative may comprise the CDRs of trastuzumab (based on Kabat numbering using abYsis software):

|  | HC CDR 1 | HC CDR2 | HC CDR3 | LC CDR1 | LC CDR2 | LC CDR3 |
|---|---|---|---|---|---|---|
| Trast-uzumab | DTYIH | RIYPTNG YTRYADS VKG | WGGDGF YAMDY | RASQD VNTAV A | SAS FLYS | QQHY TTPP T |

In particular, the antibody or fragment or derivative may comprise the CDRs of hu4-2-17 (based on Kabat numbering):

|         | HC CDR1 | HC CDR2              | HC CDR3        | LC CDR1          | LC CDR2      | LC CDR3       |
|---------|---------|----------------------|----------------|------------------|--------------|---------------|
| hu4-2-17 | SYYMS   | AIGISGN AYYASWA KS   | DHPTY GMDL     | EGNNIG SKAVH     | DDDERP S     | QVWDSS AYV    |

In particular, the antibody or fragment or derivative may comprise the CDRs of huERCS-409 (based on Kabat numbering):

|              | HC CDR1 | HC CDR2              | HC CDR3       | LC CDR1         | LC CDR2      | LC CDR3        |
|--------------|---------|----------------------|---------------|-----------------|--------------|----------------|
| huERCS-409   | SYGVI   | IIGSSGN TTYASSV KG   | YYGDS GFDS    | RASQSI GSWLS    | GASN LAS     | LGASP NGWA     |

In a preferred embodiment, the antibody or fragment or derivatives contain the variable domains of the antibodies presented in the Examples. In particular, the antibody or fragment or derivative may comprise the variable domains of trastuzumab (variable domains of SEQ ID NO. 1/2 of Table 2). In particular, the antibody or fragment or derivative may comprise the variable domains of hu4-2-17 (variable domains of SEQ ID NO. 4/5 of Table 2). In particular, the antibody or fragment or derivative may comprise the variable domains of huERCS-409 (variable domains of SEQ ID NO. 7/8 of Table 2).

Aspects of the Invention Relating to the Toxin

The ADC of the invention comprises one or two anthracycline-based small molecules ("anthracycline molecule"), wherein each anthracycline molecule is linked, via a linker comprising a peptidic sequence, to said antibody or antibody derivative at the light chain constant region C-terminus.

Anthracyclines are a highly interesting class of DNA intercalating toxins for use as payloads for ADCs because of their proven clinical validation as chemotherapeutic drugs in cancer therapy (Minotti, 2004). Anthracyclines are red-colored polyketides with high anti-tumor activity, originally derived from *Streptomyces* species. Many derivatives have been described during the last 40 years, including some that are routinely used as chemotherapy drug for various solid and hematological cancers, e.g. doxorubicin (also called adriamycin), daunorubicin, epirubicin, idarubicin, pirarubicin, zorubicin, aclarubicin, caminomycin, and valrubicine. A novel anthracycline derivative, called PNU-159682, was described as a metabolite of nemorubicin (Quintieri, 2005), which has been reported to exhibit extremely high potency for in vitro cell killing in the pico- to femtomolar range with one ovarian (A2780) and one breast cancer (MCF7) cell line (WO2012/073217).

In one embodiment, the ADC of the present invention comprises one anthracycline molecule that is linked, via a linker comprising a peptidic sequence, to said antibody or fragment or derivative at a light chain constant region C-terminus. In one embodiment, the ADC comprises two anthracycline molecules that are each linked, via a linker comprising a peptidic sequence, to said antibody or fragment or derivative at each of the two light chain constant region C-termini.

In one embodiment, at least one anthracycline-based small molecule is not doxorubicin.

In one embodiment, anthracycline-based small molecule is selected from PNU-159682, or from derivatives thereof, comprising the structure of formula (i), or derivatives thereof comprising the structure of formula (i) below. In a preferred embodiment, the toxin, joined to the linker at its wavy line, is of formula (i), as described in WO 2016/102679, which is incorporated herein by reference:

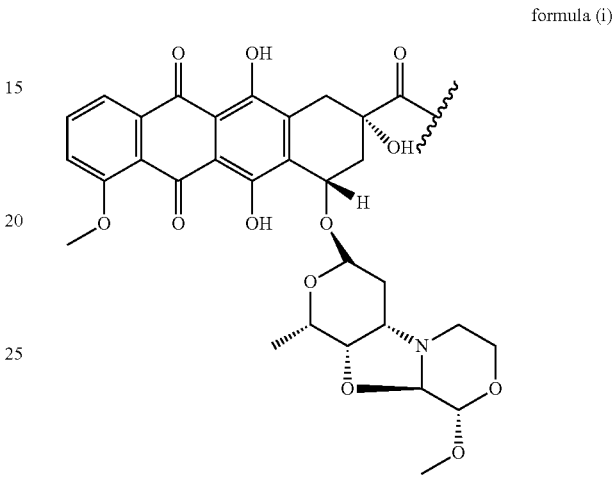

formula (i)

PNU-159682 as described in Quintieri et al. (2005).

The toxin that is not an anthracycline molecule can be a plant, fungal, or bacterial molecule. In some embodiments, the toxin that is not an anthracycline molecule is a small molecule cellular toxin, a peptide toxin, or a protein toxin. Many specific examples of these toxins are well known in the art. See, e.g., Dyba et al., Curr. Pharm. Des. 10:2311-34, 2004; Kuyucak et al., Future Med. Chem. 6:1645-58, 2014; Beraud et al., Inflamm. Allergy Drug Targets. 10:322-42, 2011; and Middlebrook et al., Microbiol. Rev. 48:199-221, 1984. In some embodiments, the toxin that is not an anthracycline molecule can be a maytansinoid (e.g., maytansinol or DM1 maytansinoid), a taxane, a calicheamicin, a cemadotin, a monomethylauristatin (e.g., monomethylauristatin E or monomethylauristatin F), or a pyrrolobenzodiazepine (PBD). The toxin that is not an anthracycline molecule can also be vincristine and prednisone. In various embodiments, toxin that is not an anthracycline molecule can be an antimetabolite (e.g., an antifolate such as methotrexate, a fluoropyrimidine such as 5-fluorouracil, cytosine arabinoside, or an analogue of purine or adenosine); mitomycin-C, dactinomycin, or mithramycin, or other non-anthracycline intercalating agents such as pyrrolobenzodiazepine; a DNA-reactive agent such as calicheamicins, tiancimycins, and other enediynes; a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an RNA polymerase inhibitor such as α-amanitin; an antimitotic agent (e.g., a vinca alkaloid such as vincristine, or a taxoid such as paclitaxel or docetaxel); a topoisomerase inhibitor (for example, etoposide, teniposide, amsacrine, topotecan); a cell cycle inhibitor (for example, a flavopyridol); or a microb-tubule agent (e.g., an epothilone, a tubulysine, a pre-tubulysine, discodermolide analog, or eleutherobin analog). The toxin that is not an anthracycline molecule can be a proteosome inhibitor, a topoisomerase inhibitor, such as bortezomib, amsacrine, etoposide, etoposide phosphate, teniposide, or doxorubicin, or a radioisotope including iodine ($^{131}$I), yttrium ($^{90}$Y), lutetium ($^{177}$Lu), actinium ($^{225}$Ac), praseodymium, astatine (At), rhenium (Re), bismuth (Bi or Bi), and rhodium (Rh).

The toxin that is not an anthracycline molecule is preferably selected from the group consisting of:
- maytansinoids, including maytansine,
- auristatins, including monomethyl auristatin MMAE, and monomethyl auristatin MMAF,
- calicheamicins,
- tubulysins
- duocarmycins
- radioisotopes
- liposomes comprising a toxic payload
- protein toxins
- taxanes, and/or
- pyrrolobenzodiazepines.

Additionally, the ADC may comprise a label or dye, notably to allow imaging. This label or dye can be least one selected from the group consisting of: a fluorescent label (including a fluorescent dye or a fluorescent protein), a chromophore label, a radioisotope label containing iodine (e.g., $^{125}$I), gallium ($^{67}$Ga), indium ($^{111}$I), technetium ($^{99m}$Tc), phosphorus ($^{32}$P), carbon ($^{14}$C), tritium ($^{3}$H), other radioisotope (e.g., a radioactive ion), and/or a protein label such as avidin or streptavidin.

Aspects of the Invention Relating to the Linker

The present invention refers to an antibody drug conjugate (ADC) comprising:
- an antibody, or antibody fragment or derivative retaining target binding properties, comprising at least one light chain constant region C-terminus, and
- an anthracycline-based small molecule, wherein the anthracycline molecule(s) is/are exclusively linked to the light chain constant region C-terminus/i of the antibody, fragment or derivative, and
wherein the anthracycline-based small molecule is linked, via a linker comprising a peptidic sequence, to said antibody, fragment or derivative.

In a preferred embodiment, said peptidic sequence of said linker comprises or consists of a peptidic motif resulting from specific cleavage of a sortase enzyme recognition motif, said sortase enzyme recognition motif preferably comprising a pentapeptide.

In a preferred embodiment, said sortase enzyme recognition motif is selected from the group consisting of: -LPXTG-, -LPXAG-, -LPXSG-, -LAXTG-, -LPXTG-, -LPXTA- and -NPQTG-, where X is any amino acid, and preferably X is E or Q.

As disclosed elsewhere herein as well as in WO2014140317, the contents of which is incorporated by reference herein, sortases (also called sortase transpeptidases) form a group of prokaryotic enzymes that modify surface proteins by recognizing and cleaving a specific sorting signal comprising a particular peptide motif. This peptide motif is also called "sortase enzyme recognition motif", "sortase recognition motif", "sortase tag" or "sortase recognition tag" herein. Usually, a given sortase enzyme has one or more sortase enzyme recognition motifs that are recognized.

Sortase enzymes can be naturally occurring, or may have undergone genetic engineering (Doerr et al., 2014). Sortase classes and their corresponding recognition sequences are generally discussed in Spirig et al. (2011). Engineered sortases, including A 2A-9 and A 4S-9 from *Staphylococcus aureus*, are described in Dorr et al. (2014) and in Chen et al. (2011).

As background and to exemplify the general concept of sortase transpeptidation, sortase A, for example, uses an oligo-glycine-stretch as a nucleophile to catalyze a transpeptidation by which the terminal amino group of the oligo-glycine effects a nucleophilic attack on the peptide bond joining the last two C-terminal residues of the sortase recognition sequence. This results in breakage of that peptide bond and the formation of a new peptide bond between the C-terminally second-to-last residue of the sortase tag and the N-terminal glycine of the oligo-glycine peptide, i.e. resulting in a transpeptidation.

The following table shows non-limiting examples of sortase enzyme recognition motifs and the resultant peptidic motifs following specific cleavage, the latter being comprised within the ADC linker (in N to C-terminal orientation):

TABLE 1

Sortase enzyme recognition sequences and peptidic motif resulting from specific cleavage, with X being any amino acid

| Sortase | Example sortase enzyme recognition sequence | Corresponding peptidic motif resulting from specific cleavage |
|---|---|---|
| Sortase of Class A, e.g., *Staphylococcus aureus* sortase A | LPXTG | LPXT |
| *Staphylococcus aureus* sortase A or engineered sortase A 4S-9 from *Staphylococcus aureus* | LPXSG | LPXS |
| *Streptococcus pyogenes* sortase A | LPXTA | LPXT |
| Sortases of Class B | NPQTN | NPQT |
| Sortases of Class C | LPLTG | LPLT |
| Sortases of Class C | LAFTG | LAFT |
| Sortases of Class D | LPNTA | LPNT |
| Engineered sortase A 2A-9 from *Staphylococcus aureus* and sortases of Class E | LAXTG | LAXT |

Figure 4A:
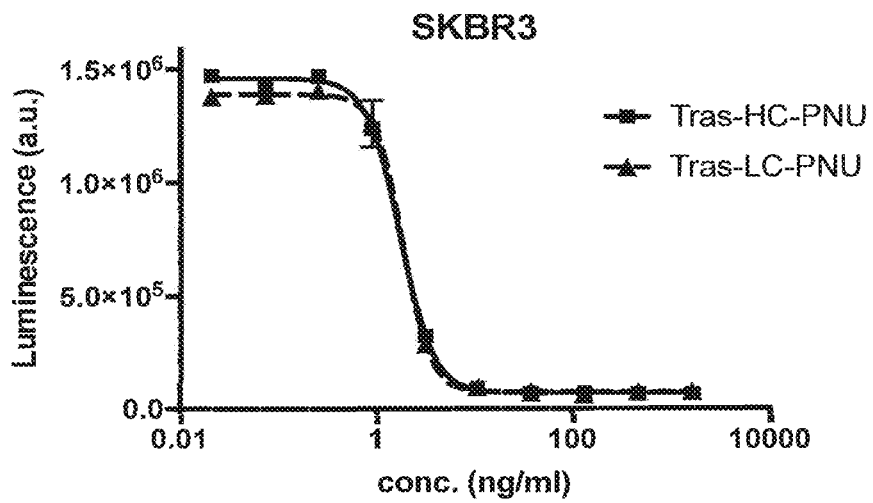
FIGS. 4A-4B show the dose-response curve of the in vitro cell killing assays on FIG. 4A SKBR3 (HER2-positive human breast cancer) and FIG. 4B Karpas-299 (HER2-negative human T cell lymphoma) cell lines with the following ADCs: Tras-HC-PNU (a HER2-targeting ADC comprising an anthracycline molecule linked to both of its heavy chain C-termini), and Tras-LC-PNU (a HER2-targeting ADC comprising an anthracycline molecule linked to both of its light chain C-termini). ADCs comprising anthracycline payloads exclusively on the heavy chain or exclusively on the light chain present comparable in vitro efficacy that is antigen mediated.

Prior to sortase conjugation, the sortase enzyme recognition motif may, at its C-terminus, furthermore carry other tags, like His-tags, Myc-tags or Strep-tags (see FIG. 4a of WO2014140317, the content of which is incorporated by reference herein). However, because the peptide bond between the 4th and 5th amino acid of the sortase enzyme recognition motif is cleaved upon sortase-mediated conjugation, these additional tags do not appear in the conjugated product.

Sortase enzyme recognition motifs may be fused the C-terminus/i of the antibody light chain by genetic fusion and are co-expressed therewith. The sortase enzyme recognition motif may be appended to the last naturally occurring C-terminal amino acid of one or both of the immunoglobulin light chains, which in case of the human immunoglobulin kappa light chain is the C-terminal cysteine residue. Said fusion or appendage can be done directly, or indirectly via additional linker elements described elsewhere herein.

We have described previously that in some cases (e.g. at the C-terminus of the Ig kappa light chains, see: Beerli et al. (2015)) it is beneficial to add additional amino acids (herein referred to as a "Spacer Sequence") between the C-terminus of the binding protein and the sortase enzyme recognition motif. This has been shown to improve sortase enzyme conjugation efficiencies of payloads to the binding protein. In the case of Ig kappa light chains, it was observed that adding 5 amino acids between the last C-terminal cysteine amino acid of the Ig kappa light chain and the sortase recognition sequence improved the kinetics of conjugation (see Beerli et al. (2015)). Therefore, it is another preferred embodiment that optionally ≥1 and ≤11 amino acids ("Spacer Sequence") are added in between the last C-terminal amino acid of the antibody and the sortase recognition sequence. In a preferred embodiment, a peptidic sequence $G_qS$, where q is preferably 1 to 10, and more preferably 4 or 5, is added in between the last light chain C-terminal amino acid and the sortase enzyme recognition motif.

In a preferred embodiment, said peptidic sequence of said linker comprises or consists of an oligoglycine sequence ("tag"), denoted $G_n$ or $Gly_n$, where n is from 1 to 21 and preferably n is 1, 2, 3, 4 or 5.

In a preferred embodiment, said peptidic sequence of said linker comprises or consists of a peptidic motif resulting from specific cleavage of a sortase enzyme recognition motif, and an oligoglycine sequence, preferably selected from the group consisting of: -LPXTG$_n$-, -LPXAG$_n$-, -LPXSG$_n$-, -LAXTG$_n$-, -LPXTG$_n$- and -NPQTG$_n$-, where X is any amino acid, and preferably X is E or Q, and where n is from 1 to 21 and preferably n is 1, 2, 3, 4 or 5. In a preferred embodiment, said peptidic sequence of said linker comprises or consists of -LPXTG$_n$- where X is any amino acid, and preferably X is E or Q, and where n is from 1 to 21 and preferably n is 1, 2, 3, 4 or 5.

In one embodiment wherein the anthracycline molecule is of formula (i), it is preferred that the linker additionally comprise an alkyldiamino group of the form $NH_2$—$(CH_2)_m$—$NH_2$, where m≥1 and ≤11, preferably m=2. In this embodiment, it is preferred that one amino group of $NH_2$—$(CH_2)_m$—$NH_2$ be directly linked at the wavy line of formula (i) to form an amide bond.

In another embodiment where the anthracycline molecule is of formula (i) and the linker additionally comprises an alkyldiamino group of the form $NH_2$—$(CH_2)_m$—$NH_2$, where m≥1 and ≤11, preferably m=2, one amino group may be linked to the wavy line of formula (i) via a linker element L1.

It is moreover preferred that the second amino group of said alkyldiamino group is linked to the oligopeptide linker, which is more preferably an oligoglycine ($Gly_n$). Preferably, the oligoglycine has a length of 1 to 21 glycine residues (i.e., n is from 1 to 21), preferably with a length of 1, 2, 3, 4 or 5 amino acids.

Visual depictions of certain non-limiting embodiments of the ADCs of the invention are given in FIG. 2.

In another embodiment, the linker may further comprises at least one further cleavable or non cleavable linker, which is preferably selected from the group consisting of: a hydrazine linker, a thiourea linker, a self-immolative linker, a succinimidyl trans-4-(maleimidylmethyl)cyclohexane-1-carboxylate (SMCC) linker, a disulfide linker, a selenoether linker, an amide linker, a thioether linker, and/or a maleimide linker.

The skilled person understands that further linkers may be suitable. Such linkers may be non-cleavable or may be cleaved by changes in pH, redox potential or specific intracellular/extracellular enzymes. Cleavable oligopeptide linkers include protease- or matrix metalloprotease-cleavable linkers. It is understood that the linker may comprise combinations of the above. For example, the linker may be a valine-citruline PAB linker.

Aspects of the Invention Relating to the Drug Antibody Ratio (DAR)

In a preferred embodiment, the ADC of the invention designed for having an anthracycline molecule linked to each light chain constant region C-terminus has a stoichiometric ratio between antibody and payload of any value between ≥1 and ≤2, and preferably of ≥1.75 and ≤2, more preferably ≥1.9 and ≤2. This ratio may also be referred to as the drug to antibody ratio ("DAR"). Methods to determine DAR are well known to the skilled person and include methods using Reverse Phase Chromatography, or HPLC-MS. It is understood that the sortase-mediated transpeptidation reaction is not 100% complete resulting in preparations of ADCs with the described DAR.

In embodiments wherein the ADC comprises additional non-anthracycline toxins, the DAR may be any value between ≥1 and ≤4.

In another preferred embodiment, the ADC of the invention designed for having an anthracycline molecule linked to only one light chain constant region C-terminus has a stoichiometric ratio between antibody and payload of any value between ≥0.5 and ≤1, and preferably of ≥0.75 and ≤1, more preferably ≥0.9 and ≤1.

Aspects of the Invention Relating to the Functional Properties

In one embodiment, the present invention refers to an antibody drug conjugate (ADC) comprising:
- an antibody, or antibody fragment or derivative retaining target binding properties, comprising at least one light chain constant region C-terminus, and
- an anthracycline-based small molecule, wherein the anthracycline molecule(s) is/are exclusively linked to the light chain constant region C-terminus/i of the antibody, fragment or derivative, and wherein the anthracycline-based small molecule is linked, via a linker comprising a peptidic sequence, to said antibody, fragment or derivative, where said ADC presents improved tolerability in vivo, preferably relative to comparable ADCs with same number and type of anthracycline molecule but in which the anthracycline molecule(s) are linked to the heavy chain constant region C-terminus or to a mixture of both heavy and light chain constant region C-termini.

Relative to this embodiment, it is preferred that tolerability is assessed relative to the mortality rate, for a given dose, over a period of 7 to 14 days in a mouse model. Relative to this embodiment, it is preferred that tolerability is assessed using a dose of ADC in the range of 2.5 to 40 mg/kg.

Whereas comparable ADCs showed very similar cell killing activity in vitro, unexpectedly, an ADC with the anthracycline linked exclusively to the light chain of the antibody showed no mortality in vivo at two tested, equivalent dose levels, compared to comparable ADCs with linkage to either exclusively the heavy chain or both heavy and light chain, the lower leading to each 1/5 dead mice, the higher leading to 5/5 dead mice (see Table 5). Similarly, in a separate experiment ADC with the anthracycline linked exclusively at the light chain were tolerated at considerably higher doses compared to ADCs with the toxin linked to only heavy or heavy and light chain. Clearly, higher tolerability as a measure for the amount which can be safely administered to a patient is beneficial for pharmaceuticals.

In one embodiment, the present invention refers to an antibody drug conjugate (ADC) comprising:
an antibody, or antibody fragment or derivative retaining target binding properties, comprising at least one light chain constant region C-terminus, and
an anthracycline-based small molecule,
wherein the anthracycline molecule(s) is/are exclusively linked to the light chain constant region C-terminus/i of the antibody, fragment or derivative, and
wherein the anthracycline-based small molecule is linked, via a linker comprising a peptidic sequence, to said antibody, fragment or derivative,
where said ADC presents a greater therapeutic index in vivo, relative to comparable ADCs with same number and type of anthracycline molecule but in which the anthracycline molecule(s) are linked to the heavy chain constant region C-terminus or to a mixture of both heavy and light chain constant region C-termini. The therapeutic index is the comparison of the amount of a therapeutic agent that causes the therapeutic effect to the amount that causes toxicity. The invention has unexpectedly shown that the same amount of toxin linked to light chain C-termini compared to heavy chain C-termini at the same dose result in higher efficacy in vivo (see FIG. 9).

In one embodiment, the present invention refers to an antibody drug conjugate (ADC) comprising:
an antibody, or antibody fragment or derivative retaining target binding properties, comprising at least one light chain constant region C-terminus, and
an anthracycline-based small molecule,
wherein the anthracycline molecule(s) is/are exclusively linked to the light chain constant region C-terminus/i of the antibody, fragment or derivative, and
wherein the anthracycline-based small molecule is linked, via a linker comprising a peptidic sequence, to said antibody, fragment or derivative,
where, for the same therapeutic efficacy, said ADC requires a decreased dosing frequency and/or a lower dose amount in vivo, preferably relative to comparable ADCs with same number and type of anthracycline molecule but in which the anthracycline molecule(s) are linked to the heavy chain constant region C-terminus or to a mixture of both heavy and light chain constant region C-termini.

In one embodiment, the present invention refers to an antibody drug conjugate (ADC) comprising:
an antibody, or antibody fragment or derivative retaining target binding properties, comprising at least one light chain constant region C-terminus, and
an anthracycline-based small molecule,
wherein the anthracycline molecule(s) is/are exclusively linked to the light chain constant region C-terminus/i of the antibody, fragment or derivative, and
wherein the anthracycline-based small molecule is linked, via a linker comprising a peptidic sequence, to said antibody, fragment or derivative,
where said ADC presents a decreased hydrophobicity, preferably relative to comparable ADCs with same number and type of anthracycline molecule but in which the anthracycline molecule(s) are linked to the heavy chain constant region C-terminus or to a mixture of both heavy and light chain constant region C-termini. Such a decreased hydrophobicity can improve ADC handling and formulation.

Pharmaceutical Compositions

In some related aspects, the invention provides pharmaceutical compositions that contain a therapeutically effective amount of the antibody drug conjugate described herein and a pharmaceutically acceptable carrier.

The pharmaceutically acceptable carrier can be one or more compatible solid or liquid fillers, diluents, other excipients, or encapsulating substances which are suitable for administration into a human or veterinary subject (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. Pharmaceutically acceptable materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

Pharmaceutical compositions of the invention can additionally contain suitable buffering agents, including, for example, acetic acid in a salt, citric acid in a salt, boric acid in a salt, and phosphoric acid in a salt. The compositions can also optionally contain suitable preservatives, such as benzalkonium chloride, chlorobutanol, parabens, and thimerosal. Pharmaceutical compositions of the invention can be presented in unit dosage form and can be prepared by any suitable method, many of which are well known in the art of pharmacy. Such methods include the step of bringing the antibody or antigen-binding fragment of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, PA.

Preparation of pharmaceutical compositions of the invention and their various routes of administration can be carried out in accordance with methods well known in the art. The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and triglycerides; hydrogel release systems; sylastic systems; peptide-based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Generally, the ADC or pharmaceutical composition of the invention is suitably packaged, e.g., in a vial, pouch, ampoule, and/or any container appropriate for a therapeutic method. Components can be provided as concentrates (including lyophilized compositions), which may be further diluted prior to use, or they can be provided at the concentration of use. For use of the ADC of the invention in vivo, single dosages may be provided in sterilized containers having the desired amount and concentration of components.

ADCs Obtained by Means and Methods of Producing ADCs

According to a first aspect, the invention refers to an antibody drug conjugate (ADC) comprising:

an antibody, or antibody fragment or derivative retaining target binding properties, comprising at least one light chain constant region C-terminus, and an anthracycline-based small molecule, wherein the anthracycline molecule(s) is/are exclusively linked to the light chain constant region C-terminus/i of the antibody, fragment or derivative, and wherein the anthracycline-based small molecule is linked, via a linker comprising a peptidic sequence, to said antibody, fragment or derivative.

In one embodiment, the antibody drug conjugate of the invention is obtainable by means of site-specific sortase-enzyme mediated conjugation of:

a) an antibody or fragment or derivative carrying a sortase enzyme recognition motif at the light chain C-termini, and b) one or more anthracycline-based small molecules each carrying an oligoglycine tag.

The invention also refers to a method of producing an ADC of the invention, which method comprises the following steps:

a) providing an antibody or antibody derivative carrying asortase enzyme recognition motif at the light chain C-terminus/i, b) providing one or more anthracycline-based small molecules each carrying an oligoglycine tag, and c) conjugating the antibody or antibody derivative and the one or more anthracycline-based small molecules by means of sortase-mediated conjugation using a sortase enzyme that recognizes said sortase enzyme recognition motif.

Preferably, in all embodiments discussed herein, the sortase enzyme recognition motif is provided exclusively at the light chain C-terminus/i.

It is important to understand that, in all embodiments discussed herein (where *Streptococcus pyogenes* sortase A is used), the oligo-glycine $Gly_n$ can optionally be replaced by an oligo-alanine $Ala_n$.

All previously mentioned limitations with regards to the antibody or fragment or derivative, the anthracycline-based small molecules, the linker and the sortase, as well as any other limitations referred to herein, represent preferred embodiments of the embodiments referring to the ADC of the invention is obtained by means of site-specific sortase-enzyme mediated conjugation and to methods of producing an ADC.

Medical Uses and Methods of Treatment

The present invention further refers to an ADC, as described herein, for use in the treatment of a subject that is suffering from, at risk of developing, and/or diagnosed with a neoplastic disease.

The present invention also refers to an ADC, as described herein, for use in the treatment of a subject that is suffering from, at risk of developing, and/or diagnosed with an immune disease or disorder. Alternatively, a method for treating a patient suffering from, at risk of developing, and/or being diagnosed for a neoplastic disease is provided, which method comprises the administration of an antibody drug conjugate according the above description in a therapeutically effective amount or dosage.

The terms "treating" or "treatment" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated. In particular, the treatment may be administered as an intravenous infusion.

In one embodiment, the ADC is administered as a monotherapy. In an alternative embodiment, the ADC, is administered with or in parallel to further therapeutic agents.

In particular, the ADC may be administered at a dosage of about 0.1-20 mg/kg.

The term "subject" refers to human and non-human animals (especially non-human mammals), and preferably to human animals.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus (with the exception of FIG. 1, wherein the orientation is depicted as C- to N-terminal); all nucleic acid sequences disclosed herein are shown 5'→3'.

Example 1: Antibody Expression and Purification

Expression vectors: Fab sequences determined above to bind human CS1 were codon-optimized for human expression; variable domains were synthesized as DNA by GenScript (Piscataway, USA) and included within an expression vector containing suitable restriction sites and the appropriate constant domain (as per Waldmeier et al. 2016 for expression in HEK293T cells, and as per Beerli et al. 2015 for expression in CHO cells).

HEK Expression and Purification:

Expression vectors were transfected into HEK293T cells using Lipofectamine® LTX Reagent with PLUS™ Reagent (Thermo Fisher Scientific, Reinach, Switzerland, 15388100); following a 1-day incubation (37° C., 5% CO$_2$, growth media: Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept, Allschwil, Switzerland)), cells were expanded under selection conditions (2 μg/mL of puromycin (Sigma-Aldrich, Buchs SG, Switzerland, P8833-25 mg stock at 2 mg/mL)). Cells were split and further expanded (37° C., 5% CO$_2$); once confluency was reached, tissue culture dishes were coated with 20 μg/ml poly-L-Lysine (Sigma-Aldrich, P1524) for 2 hrs at 37° C. and washed twice with PBS. Then, cells were trypsinized and split 1:3 onto poly-L-lysine-coated plates. After reaching confluency, cells were washed with PBS followed by media replacement to production media (DMEM/F-12, Gibco/Thermo Fisher Scientific, 31330-03) supplemented with 1 μg/mL puromycin (Sigma, P8833), 100 IU/mL of Pen-Strep-Fungizone (Bioconcept), 161 μg/mL of N-acetyl-L-cysteine (Sigma-Aldrich, A8199) and 10 μg/mL of L-glutathione reduced (Sigma-Aldrich, G6529). Supernatant, harvested bi-weekly and filtered (0.22 μm) to remove cells, was stored at 4° C. until purification.

For purification, filtered supernatant was loaded onto a PBS-equilibrated Protein A column and washed with PBS; elution was performed using 0.1 M glycine (pH 2.5) on an ÄKTA pure (GE Healthcare). Fractions were immediately neutralized with 1 M Tris-HCl buffer (pH 8.0) and analyzed for protein purity and integrity by SDS-PAGE. Protein-containing fractions were pooled and subjected to buffer exchange using Amicon filtration units (Millipore, Schaffhausen, Switzerland, UFC901008) to reach a dilution of 1:100, and then sterile filtered using a low retention filter (0.20 μm, Carl Roth, Karlsruhe, Germany, PA49.1).

CHO expression and purification: Expression vectors encoding each of the full-length heavy and light chains were assembled in mammalian expression vector. Antibodies were transiently expressed in CHO cells by methods known in the art and recombinant antibodies were purified by standard protein A purification from CHO cell supernatants, as known in the art. In short, the CHO cell supernatants were harvested by centrifugation and sterile filtered (0.2 μm) before FPLC-based affinity purification using protein A columns. Bound antibody was eluted in 0.1 M glycine (pH 2.5 to 3.5) and immediately neutralized with 1 M Tris-HCl buffer (pH 7.5). Buffer exchange to desired final formulation buffer was performed as known in the art (e.g. Dialysis or TFF). The purity and integrity of the recombinant antibodies was analyzed by SDS-PAGE, SEC and MS.

TABLE 2

Antibody amino acid sequences of the Examples

| SEQ ID NO. Name | Amino Acid Sequence (with constant domain underlined, CDRs identified based on the Kabat system using abYsis software, Swindells et al., 2017, in bold) HC: heavy chain, LC: light chain |
|---|---|
| SEQ ID NO. 1 Trastuzumab HC (K467R mutation) | EVQLVESGGGLVQPGGSLRLSCAASGFNIKDTYIHWVRQAPGKGLEWVARIYPT NGYTRYADSVKGRFTISADTSKNTAYLQMNSLRAEDTAVYYCSRWGGDGFYA MDYWGQGTLVTVSS<u>ASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHEAL HNHYTQKSLSLSPGR</u> |
| SEQ ID NO. 2 Trastuzumab LC | DIQMTQSPSSLSASVGDRVTITCRASQDVNTAVAWYQQKPGKAPKLLIYSASFLY SGVPSRFSGSRSGTDFTLTISSLQPEDFATYYCQQHYTTPPTFGQGTKVEIK<u>RTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC</u> |
| SEQ ID NO. 3 Trastuzumab HC | EVQLVESGGGLVQPGGSLRLSCAASGFNIKDTVIHWVRQAPGKGLEWVARIYPT NGYTRYADSVKGRFTISADTSKNTAYLQMNSLRAEDTAVYYCSRWGGDGFYA MDYWGQGTLVTVSS<u>ASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVDVSH</u> |

TABLE 2-continued

Antibody amino acid sequences of the Examples

| SEQ ID NO. Name | Amino Acid Sequence (with constant domain underlined, CDRs identified based on the Kabat system using abYsis software, Swindells et al., 2017, in bold) HC: heavy chain, LC: light chain |
|---|---|
| | EDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHEAL HNHYTQKSLSLSPGK |
| SEQ ID NO. 4 hu4-2-17 HC | QVQLRESGPGLVKPSETLSLTCTVSGFDISSYYMSWVRQPPGKGLEWIGAIGISGN AYYASWAKSRVTISRDTSKNQFSLKLSSVTAADTAVYYCARDHPTYGMDLWGP GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKS LSLSPGK |
| SEQ ID NO. 5 hu42-17 LC | SYELTQPPSVSVAPGKTARITCEGNNIGSKAVHWYQQKPGQAPVLVIYDDDERPS GIPERFSGSNSGNTATLTISRVEAGDEADYYCQVWDSSAYVFGGGTKLTVLGQPK AAPSVTLFPPSSEELQANKATLVCLISDFYPGAVTVAWKADSSPVKAGVETTTPSK QSNNKYAASSYLSLTPEQWKSHKSYSCQVTHEGSTVEKTVAPTECS |
| SEQ ID NO. 6 hu4-2-17 HC (K467R mutation) | QVQLRESGPGLVKPSETLSLTCTVSGFDISSYYMSWVRQPPGKGLEWIGAIGISGN AYYASWAKSRVTISRDTSKNQFSLKLSSVTAADTAVYYCARDHPTYGMDLWGP GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKS LSLSPGR |
| SEQ ID NO. 7 huERCS-409 HC | EQQVVESGGGLVQPGGSLRLSCAVSGFSLNSYGVIWVRQAPGKGLEYVSIIGSSG NTYYASSVKGRFTISRDTRLNTVYLQMNSLRAEDTAVYFCARYYGDSGFDSWG QGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGK |
| SEQ ID NO. 8 huERCS-409 LC | DQQLTQSPSSLSASVGDRVTITCRASQSIGSWLSWYQQKPGKAPKWYGASNLA SGVPSRFSGSRSGTDYTLTISSLQPEDFATYYCLGASPNGWAFGQGTKVEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| SEQ ID NO. 9 huERCS-409 HC (K467R mutation) | EQQVVESGGGLVQPGGSLRLSCAVSGFSLNSYGVIWVRQAPGKGLEYVSIIGSSG NTYYASSVKGRFTISRDTRLNTVYLQMNSLRAEDTAVYFCARYYGDSGFDSWG QGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGR |
| SEQ ID NO. 10 Ac10 HC | QIQLQQSGPEVVKPGASVKISCKASGYTFTDYYITWVKQKPGQGLEWIGWIYPGS GNTKYNEKFKGKATLTVDTSSSTAFMQLSSLTSEDTAVYFCANGYNYWFAYW GQGTQVTVSAASTKGPSVFPLAPSSKSTSGGTAALGCLVKDYFPEPVTVSWNSGA LTSGVHTFPAVLQSSGLYSLSSVVTVPSSSLGTQTYICNVNHKPSNTKVDKKVEPK SCDKTHTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSNKA LPAPIEKTISKAKGQPREPQVYTLPPSRDELTKNQVSLTCLVKGFYPSDIAVEWESN GQPENNYKTTPPVLDSDGSFFLYSKLTVDKSRWQQGNVFSCSVMHEALHNHYTQ KSLSLSPGK |
| SEQ ID NO. 11 Ac10 LC | DIVLTQSPASLAVSLGQRATISCKASQSVDFDGDSYMNWYQQKPGQPPKVLIYA ASNLESGIPARFSGSGSGTDFTLNIHPVEEEDAATYYCQQSNEDPWTFGGGTKLEI KRTVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |

Table 3 lists the protocols used for expression and purification of antibody batches used in the subsequent examples, along with their final concentration and buffer.

3B, and 3C respectively). The identity and the purity of the glycine-modified toxins was confirmed by mass-spectrometry and HPLC. Each of the Gly-modified toxins exhibited

TABLE 3

Protocols used for expression and purification of antibody batches used in the Examples

| Antibody (ref.) | Antibody SEQ ID HC/LC | C-Terminal Tags (HC: Heavy Chain, LC: Light Chain) | CHO/HEK | Buffer |
|---|---|---|---|---|
| Tras (mab183) | HC: SEQ ID NO. 1<br>LC: SEQ ID NO. 2 | HC: LPETG-Strep<br>LC: G$_4$SLPETG-Strep | CHO | PBS with 100 mM L-arginine |
| Tras-HC (mab090) | HC: SEQ ID NO. 3<br>LC: SEQ ID NO. 2 | HC: LPETG-Strep<br>LC: none | CHO | PBS |
| Tras-LC (mab106) | HC: SEQ ID NO. 3<br>LC: SEQ ID NO. 2 | HC: none<br>LC: G$_4$SLPETG-Strep | CHO | PBS |
| Tras (mab302) | HC: SEQ ID NO. 1<br>LC: SEQ ID NO. 2 | HC: LPETG-Strep<br>LC: G$_4$SLPETG-Strep | HEK | PBS |
| Tras-HC (mab364) | HC: SEQ ID NO. 3<br>LC: SEQ ID NO. 2 | HC: LPETG-Strep<br>LC: none | HEK | PBS |
| Tras-LC (mab363) | HC: SEQ ID NO. 3<br>LC: SEQ ID NO. 2 | HC: none<br>LC: G$_4$SLPETG-Strep | HEK | PBS |
| hu4-2-17 mab321 | HC: SEQ ID NO. 6<br>LC: SEQ ID NO. 5 | HC: LPETG-Strep<br>LC: G$_4$SLPETG-Strep | CHO | PBS |
| hu4-2-17 mab339 | HC: SEQ ID NO. 6<br>LC: SEQ ID NO. 5 | HC: LPETG-Strep<br>LC: none | CHO | PBS |
| hu4-2-17 mab338 | HC: SEQ ID NO. 4<br>LC: SEQ ID NO. 5 | HC: none<br>LC: G$_4$SLPETG-Strep | CHO | PBS |
| huERC S-409 (mab325) | HC: SEQ ID NO. 9<br>LC: SEQ ID NO. 8 | HC: LPETG-Strep<br>LC: G$_4$SLPETG-Strep | HEK | PBS |
| huERC S-409-HC (mab331) | HC: SEQ ID NO. 9<br>LC: SEQ ID NO. 8 | HC: LPETG-Strep<br>LC: none | HEK | PBS |
| huERC S-409-LC (mab332) | HC: SEQ ID NO. 7<br>LC: SEQ ID NO. 8 | HC: none<br>LC: G$_4$SLPETG-Strep | HEK | PBS |
| hu4-2-17 (mab405) | HC: SEQ ID NO. 6<br>LC: SEQ ID NO. 5 | HC: LPETG-TwinStrep<br>LC: G$_4$SLPETG-TwinStrep | CHO | 20 mM Histidine, pH 6.5, 150 mM NaCl |
| hu4-2-17 (mab461) | HC: SEQ ID NO. 6<br>LC: SEQ ID NO. 5 | HC: LPQTGG<br>LC: none | CHO | 20 mM Histidine, pH 6.5, 150 mM NaCl |
| hu4-2-17 (mab462) | HC: SEQ ID NO. 6<br>LC: SEQ ID NO. 5 | HC: none<br>LC: G4SLPQTGG | CHO | 20 mM Histidine, pH 6.5, 150 mM NaCl |
| Ac10-HC (mab341) | HC: SEQ ID NO. 10<br>LC: SEQ ID NO. 11 | HC: LPETG-TwinStrep<br>LC: none | CHO | PBS |
| Ac10-LC (mab340) | HC: SEQ ID NO. 10<br>LC: SEQ ID NO. 11 | HC: none<br>LC: G$_4$SLPETG-TwinStrep | CHO | PBS |

Sortase A. Recombinant and affinity purified Sortase A enzyme from *Staphylococcus aureus* was produced in *E. coli* as disclosed in WO2014140317A1.

Figure 3A:
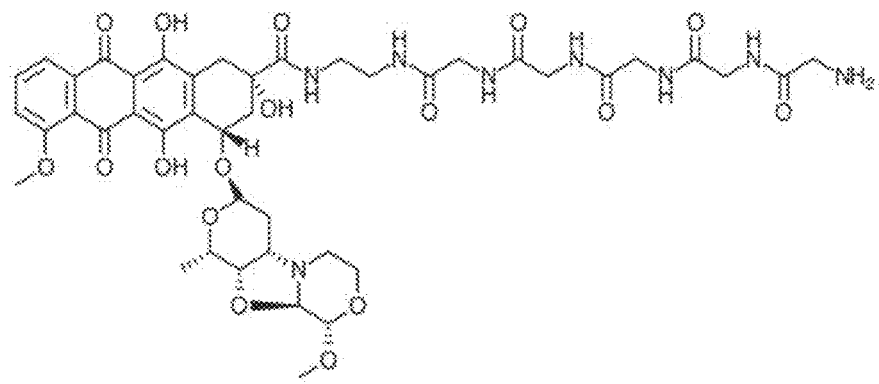
FIG. 3A depicts a pentaglycine-modified PNU derivative (G5-PNU), FIG. 3B a triglycine-modified PNU derivative (G3-PNU) and FIG. 3C a diglycine-modified PNU derivative (G2-PNU), as used in the Examples.
Figure 3B:
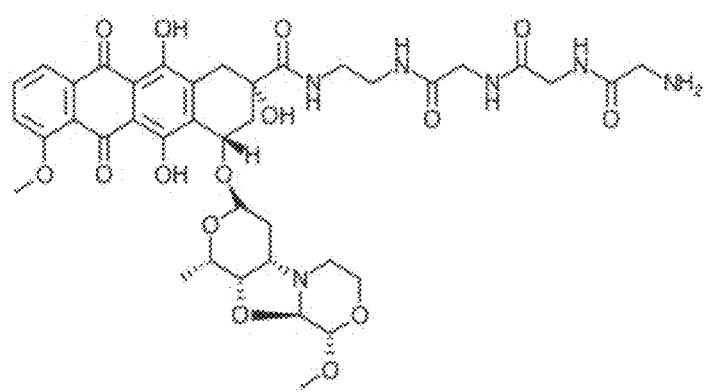
Figure 3C:
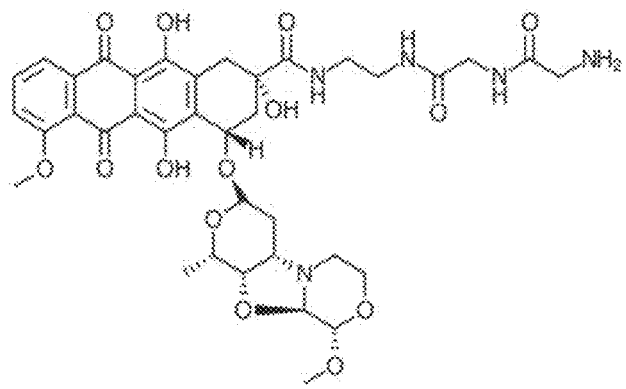

Generation of glycine-modified toxins. Pentaglycine-modified EDA-anthracycline derivative (G5-PNU), triglycine-modified EDA-anthracycline derivative (G3-PNU) and diglycine-modified EDA-anthracycline derivative (G2-PNU) were manufactured by Concortis/Levena (FIGS. 3A, >95% purity as gauged by a single peak in the HPLC chromatogram.

Sortase-mediated antibody conjugation. The above-mentioned toxins were conjugated to antibodies as per Table 4 by incubating tagged mAbs [10 μM] with glycine modified toxin [200 μM] and 3-40/1 Sortase A in conjugation buffer (50 mM HEPES, pH 7.5, 1 mM CaCl$_2$, 150 mM NaCl, 10% by vol. glycerol) for at least 3.5 h at 25° C. The reaction was stopped by passing it through a Protein A column (rProtein A Gravitrap column, GE Healthcare). Bound conjugate was eluted with 5 column volumes of elution buffer (0.1 M glycine pH 2.5, 50 nM NaCl), with 1 column volume fractions collected into tubes containing up to 25% v/v 1M Tris- or HEPES (pH 8) base to neutralise the acid. Protein containing fractions were pooled and formulated in the formulation buffer of Table 4.

ADC analytics. DAR was assessed by Reverse Phase Chromatography performed on a Polymer Labs PLRP 2.1 mm×5 cm, 5 μm column run at 1 mL/min/80° C. with a 25-minute linear gradient between 0.05 and 0.1% TFA/$H_2O$ and 0.04 to 0.1% TFA/$CH_3CN$. Samples were first reduced by incubation with DTT at pH 8.0 at 37° C. for 15 minutes. The DAR determined by Reverse Phase Chromatography is summarized in Table 4 below.

TABLE 4

Protocols used for generation of ADCs used in the Examples

| ADC (ref.) | mAb (ref.) | Toxin | Formulation Buffer | DAR |
|---|---|---|---|---|
| Tras-PNU (adc424) | mab183 | G5-PNU | 10 mM Succinate pH 5.0, 175 mM Sucrose 0.02% Tween 20 | 3.90 |
| Tras-HC-PNU (adc421) | mab090 | G5-PNU | 10 mM Succinate pH 5.0, 175 mM Sucrose 0.02% Tween 20 | 1.96 |
| Tras-LC-PNU (adc422) | mab106 | G5-PNU | 10 mM Succinate pH 5.0, 175 mM Sucrose 0.02% Tween 20 | 1.95 |
| Tras-PNU (adc667) | mab302 | G3-PNU | 10 mM Succinate pH 5.0, 175 mM Sucrose 0.02% Tween 20 | 3.90 |
| Tras-HC-PNU (adc668) | mab364 | G3-PNU | 10 mM Succinate pH 5.0, 175 mM Sucrose 0.02% Tween 20 | 1.96 |
| Tras-LC-PNU (adc669) | mab363 | G3-PNU | 10 mM Succinate pH 5.0, 175 mM Sucrose 0.02% Tween 20 | 1.97 |
| hu4-2-17-PNU (adc519) | mab321 | G3-PNU | 15 mM Histidine, pH 6.5, 175 mM Sucrose, 0.02% Tween20 | 3.91 |
| hu4-2-17-HC-PNU (adc520) | mab339 | G3-PNU | 15 mM Histidine, pH 6.5, 175 mM Sucrose, 0.02% Tween20 | 1.98 |
| hu4-2-17-LC-PNU (adc521) | mab338 | G3-PNU | 15 mM Histidine, pH 6.5, 175 mM Sucrose, 0.02% Tween20 | 1.96 |
| huERCS-409-PNU (adc489) | mab325 | G3-PNU | 15 mM Histidine, pH 6.5, 175 mM Sucrose, 0.02% Tween20 | 3.89 |
| huERCS-409-HC-PNU (adc490) | mab331 | G3-PNU | 15 mM Histidine, pH 6.5, 175 mM Sucrose, 0.02% Tween20 | 1.98 |
| huERCS-409-LC-PNU (adc522) | mab332 | G3-PNU | 15 mM Histidine, pH 6.5, 175 mM Sucrose, 0.02% Tween20 | 1.83 |
| hu4-2-17-PNU (adc828) | mab405 | G2-PNU | 15 mM Histidine pH 6.5, 175 mM Sucrose, 0.02% Tween20 | 3.92 |
| hu4-2-17-HC-PNU (adc822) | mab461 | G2-PNU | 15 mM Histidine pH 6.5, 175 mM Sucrose, 0.02% Tween20 | 1.98 |
| hu4-2-17-LC-PNU (adc826) | mab462 | G2-PNU | 15 mM Histidine pH 6.5, 175 mM Sucrose, 0.02% Tween20 | 1.98 |
| Tras-LC-PNU (adc588) | mab363 | G3-PNU | 10 mM Succinate pH 5.0, 175 mM Sucrose 0.02% Tween 20 | 1.92 |
| Tras-HC-PNU (adc589) | mab364 | G3-PNU | 10 mM Succinate pH 5.0, 175 mM Sucrose 0.02% Tween 20 | 1.97 |
| Ac10-HC-PNU (adc782) | mab341 | G3-PNU | PBS | 1.97 |
| Ac10-LC-PNU (adc611) | mab340 | G3-PNU | PBS | 1.93 |
| huERCS-409-LC-PNU (adc572) | mab356 | G3-PNU | 15 mM Histidine pH 6.5, 175 mM Sucrose, 0.02% Tween20 | 1.89 |
| huERCS-409-HC-PNU (adc758) | mab404 | G3-PNU | 15 mM Histidine pH 6.5, 175 mM Sucrose, 0.02% Tween20 | 1.97 |
| huERCS-409-LC-PNU (adc763) | mab422 | G2-PNU | 15 mM Histidine pH 6.5, 175 mM Sucrose, 0.02% Tween20 | 1.89 |
| huERCS-409-HC-PNU (adc762) | mab421 | G2-PNU | 15 mM Histidine pH 6.5, 175 mM Sucrose, 0.02% Tween20 | 1.94 |
| hu4-2-17-LC-PNU (adc573) | mab357 | G3-PNU | 15 mM Histidine pH 6.5, 175 mM Sucrose, 0.02% Tween20 | 1.92 |
| hu4-2-17-HC-PNU (adc759) | mab406 | G3-PNU | 15 mM Histidine pH 6.5, 175 mM Sucrose, 0.02% Tween20 | 1.97 |
| hu4-2-17-LC-PNU (adc761) | mab420 | G2-PNU | 15 mM Histidine pH 6.5, 175 mM Sucrose, 0.02% Tween20 | 1.92 |
| hu4-2-17-HC-PNU (adc760) | mab419 | G2-PNU | 15 mM Histidine pH 6.5, 175 mM Sucrose, 0.02% Tween20 | 1.91 |

Example 2

All tolerability assessments were conducted at Aurigon. The ADCs of Table 5 (formulated in PBS) were administered at the indicated doses twice over 14 days (on days 1 and 8, by intravenous administration via bolus) to groups of five CD-1 female mice (5-6 weeks old; from Charles River, Sulzfeld, Germany). Mice were housed in groups of 5 animals per cage and were provided water and pellets ad libitum. Parameters monitored twice daily throughout the study included mortality and cage-side clinical observations.

TABLE 5

Mortality of mice treated with ADCs

| | Mortality at day 14 (relative to 5 initial mice per group) Dose levels [mg/kg] | |
|---|---|---|
| ADC | 3 | 10 |
| Tras-PNU (adc424) | 1/5 | 5/5 |
| Tras-HC-PNU (adc421) | 1/5 | 5/5 |
| Tras-LC-PNU (adc422) | 0/5 | 0/5 |

The results of Table 5 lay forth a significantly lower mortality rate at equivalent ADC dose of mice treated with ADC comprising the anthracycline payload at the light chain C-termini (Tras-LC-PNU) relative to mice treated with ADC comprising the anthracycline payload at the heavy chain C-termini (Tras-HC-PNU) or with ADC comprising the anthracycline payload at both heavy and light chain C-termini (Tras-PNU).

Example 3

The ADCs of Table 6 (formulated in PBS) were administered at the indicated doses on day 1 (by intravenous administration via bolus) to groups of three CD-1 female mice (4-6 weeks old; from Charles River, Sulzfeld, Germany) and were observed for 14 days (for 2.5 and 5 mg/kg doses) or for 28 days (for 10, 15 and 20 mg/kg doses). Mice were housed in groups of 3 animals per cage and were provided water and pellets ad libitum. Parameters monitored twice daily throughout the study included mortality and cage-side clinical observations.

TABLE 6

Mortality of mice treated with ADCs

| ADC | Mortality at day 14 or 28 (relative to 3 initial mice per group) Dose levels [mg/kg] | | | | |
|---|---|---|---|---|---|
| | 2.5 | 5 | 10 | 15 | 20 |
| Tras-PNU (adc667) | 0/3 | 2/3 (group 1) 3/3 (group 2) | — | — | — |
| Tras-HC-PNU (adc668) | 0/3 | 0/3 | 3/3 | — | — |
| Tras-LC-PNU (adc669) | — | 0/3 | 0/3 | 1/3 | 3/3 |

The results of Table 6 lay forth a significantly lower dose causing mortality of mice treated with ADC comprising the anthracycline payload at the heavy chain C-termini (Tras-HC-PNU) or with ADC comprising the anthracycline payload at both heavy and light chain C-termini (Tras-PNU), as opposed to mice treated with ADC comprising the anthracycline payload at the light chain C-termini (Tras-LC-PNU).

Example 4

Cytotoxicity of the HER2-targeting ADCs of Table 7 was investigated using the HER2-positive human SKBR3 cell line. HER2-negative human cell line Karpas-299 was used as control. For this, 5000 SKBR3 and 5000 Karpas-299 cells, per well, were each plated on 96-well plates (excluding edge wells, which contained water) in 75⨰ DMEM or RPMI, respectively, supplemented with 10% by vol. FCS, 100 IU/mL Pen-Strep-Fungizone and 2 mM L-Glutamine at a density of $6.66 \times 10^4$ cells per well, and were grown at 37° C. in a humidified incubator at 5% $CO_2$ atmosphere. After a 1-day incubation, each ADC was added to respective wells in an amount of 25⨰ of 3.5-fold serial dilutions in growth medium (starting ADC concentration of 80 µg/mL, giving final ADC concentrations ranging from 20 µg/ml to 0.89 ng/ml). After 4 additional days, plates were removed from the incubator and equilibrated to room temperature. After approximately 30 min, 50⨰ of CellTiter-Glo® 2.0 Luminescent Solution (Promega, G9243) was added to each well. After shaking the plates at 750 rpm for 5 min followed by 10 min incubation without shaking, luminescence was measured on a Spark 10M plate reader with an integration time of 1 second per well. Curves of luminescence versus ADC concentration (ng/mL) were fitted with Graphpad Prism Software. The $IC_{50}$ values, determined using the built-in "log(inhibitor) vs. response—Variable slope (four parameters)" $IC_{50}$ determination function of Prism Software, are reported in Table 7.

TABLE 7

In vitro cell killing by ADCs (ng/mL)

| | Cell type | |
|---|---|---|
| ADC | SKBR3 | Karpas-299 |
| HER2 expression status | Positive | Negative |
| Tras-HC-PNU (adc668) | 1.7 | 27'000 |
| Tras-LC-PNU (adc669) | 1.8 | 48'000 |

Figure 4B:
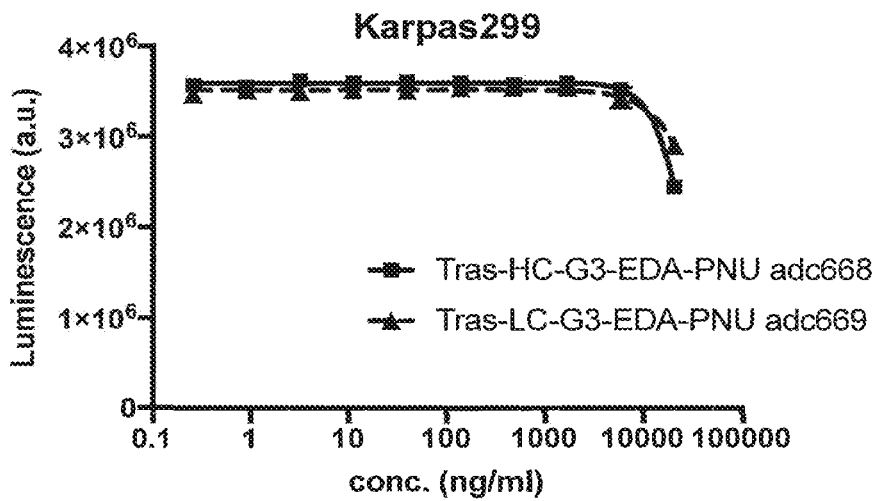

FIG. 4 shows the dose-response curve of the in vitro cell killing assays on the SKBR3 and Karpas-299 cell lines with the ADCs of Table 7. As per the Figure and Table, comparable ADCs comprising anthracycline payloads exclusively on the heavy chain or exclusively on the light chain present comparable in vitro efficacy.

Example 5

Cytotoxicity of the HER2-targeting ADCs of Table 8 was investigated using the HER2-positive human SKOV3 cell line. A comparable CD30-targeting ADC was used as isotype control. For this, the protocol of Example 4 was followed but plating 2'000 SKOV3 cells per well were plated on 96-well plates (excluding edge wells, which contained water) in 75⨰ DMEM supplemented with 10% by vol. FCS, 100 IU/mL Pen-Strep-Fungizone and 2 mM L-Glutamine at a density of $2.66 \times 10^4$ cells per well.

TABLE 8

In vitro cell killing by ADCs (ng/mL)

| ADC | Cell type SKOV3 |
|---|---|
| HER2 expression status | Positive |
| Tras-HC-PNU (adc589) | 4.4 |
| Tras-LC-PNU (adc588) | 4.6 |
| Ac10-HC-PNU (adc782) | 10000 |
| Ac10-LC-PNU (adc611) | 10000 |

Figure 5:
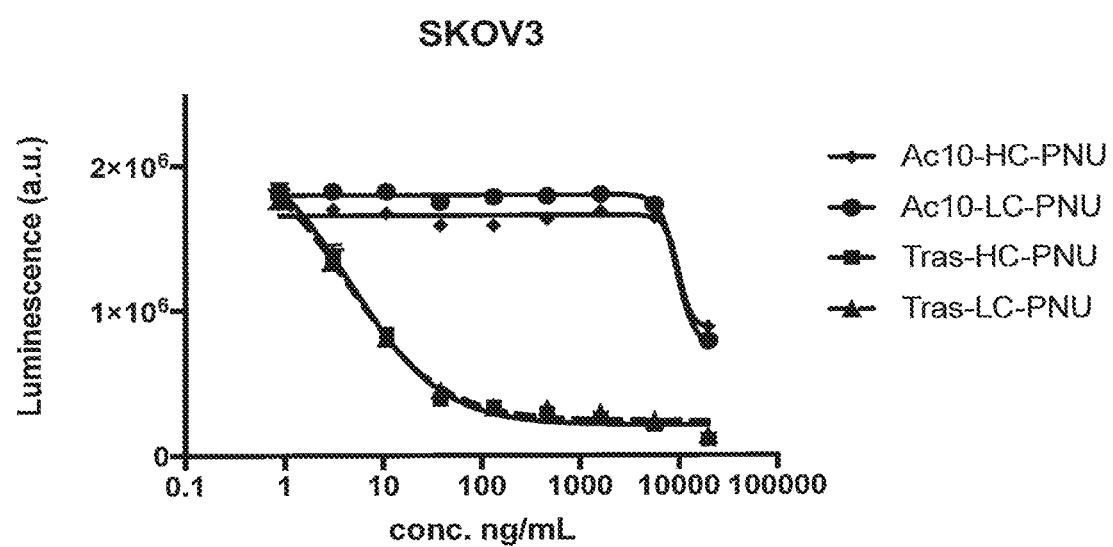
FIG. 5 shows the dose-response curve of the in vitro cell killing assays on the SKOV3 (HER2-positive human ovarian cancer) cell line with the following ADCs: Tras-HC-PNU (a HER2-targeting ADC comprising an anthracycline molecule linked to both of its heavy chain C-termini), and Tras-LC-PNU (a HER2-targeting ADC comprising an anthracycline molecule linked to both of its light chain C-termin), Ac10-HC-PNU (a CD30-targeting ADC comprising an anthracycline molecule linked to both of its heavy chain C-termini), and Ac10-LC-PNU (a CD30-targeting ADC comprising an anthracycline molecule linked to both of its light chain C-termini). ADCs comprising anthracycline payloads exclusively on the heavy chain or exclusively on the light chain present comparable in vitro efficacy that is antigen mediated.

FIG. 5 shows the dose-response curve of the in vitro cell killing assays on the SKOV3 cell line with the ADCs of Table 8. As per the Figure and Table, comparable ADCs comprising anthracycline payloads exclusively on the heavy chain or exclusively on the light chain present comparable in vitro efficacy and antigen-mediated.

Example 6

The ADCs of Table 9 (formulated in PBS) were administered at the indicated doses on day 1 (by intravenous administration via bolus) to groups of three or six CD-1 female mice (4-6 weeks old; from Charles River, Sulzfeld, Germany) and were observed for 7-10 days. Mice were housed in groups of 3 animals per cage and were provided water and pellets ad libitum. Parameters monitored twice daily throughout the study included mortality and cage-side clinical observations.

TABLE 9

Mortality of mice treated with ADCs

| Test item | Mortality by day 7-10 (relative to 3 or 6 initial mice per group) | | | | | |
|---|---|---|---|---|---|---|
| Dose levels [mg/kg] | 2.5 | 5 | 10 | 15 | 20 | 40 |
| huERCS-409-PNU (adc489) | 2/3 (group 1) 3/3 (group 2) | — | — | — | — | — |
| huERCS-409-HC-PNU (adc490) | 1/3 | 2/3 (group 1) 6/6 (group 2) | — | — | — | — |
| huERCS-409-LC-PNU (adc522) | — | 0/3 | 0/3 | 1/3 | 3/3 | — |
| hu4-2-17-PNU (adc519) | 0/3 | 3/3 | — | — | — | — |
| hu4-2-17-HC-PNU (adc520) | 0/3 | 1/3 | 3/3 | — | — | — |
| hu4-2-17-LC-PNU (adc521) | — | 0/3 | 0/3 | — | 0/3 | 3/3 |

The results of Table 9 lay forth a significantly lower dose causing mortality of mice treated with ADC comprising the anthracycline payload at the heavy chain C-termini or with ADC comprising the anthracycline payload at both heavy and light chain C-termini, as opposed to mice treated with ADC comprising the anthracycline payload at the light chain C-termini.

Example 7

The ADCs of Table 10 (formulated in PBS) were administered at 1 mg/kg (by single intravenous administration via bolus) to groups of 15 Swiss female outbred CD1 mice (body weights of 21-26 g; from Janvier, Saint Berthevin, France; allocated to groups by simple random allocation). Mice were housed in groups of 3 animals per cage and were provided water and pellets ad libitum. Groups of 3 mice per treatment group were euthanized by terminal bleed following deep anesthesia at 1 hour, 24 hours, 3 days, 7 days and 14 days from ADC administration. Serum from a given group and timepoint was collected for analysis by ELISA.

Figure 6:
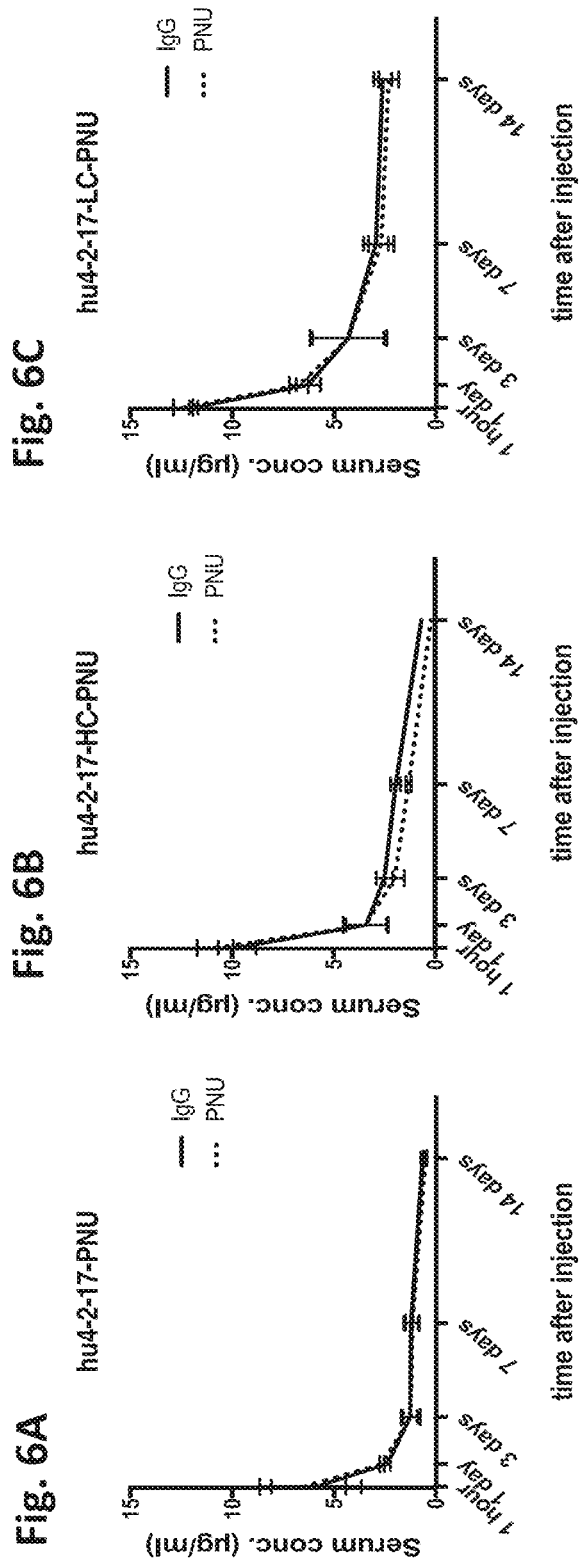
FIGS. 6A-6B show the serum concentration of the ADC IgG and anthracycline toxin over time in female CD1 mice treated with FIG. 6A hu4-2-17-PNU (a ROR1-targeting ADC with anthracycline payloads linked to both heavy and light chain C-termini), FIG. 6B hu4-2-17-HC-PNU (a ROR1-targeting ADC with anthracycline payloads linked to its heavy chain C-termini), or FIG. 6C hu4-2-17-LC-PNU (a ROR1-targeting ADC with anthracycline payloads linked to its light chain C-termini).

Dilution series of serum samples (dilution factor 3.5) were captured on ELISA plates coated with 2 µg/ml huROR1 antigen. The bound ADC was detected with an in-house developed mouse anti-PNU mAb (generated by immunizing mice with a human IgG-PNU conjugate and screening with a BSA-PNU conjugate), while the bound total IgG was detected with a 1:2500 dilution of an HRP-conjugated donkey anti-human IgG (Jackson Immunoresearch, 709-035-149). Serum concentrations of ADC and total IgGs were calculated from half maximal values of the sample titrations by comparison with a sample of the same ADC of known concentration. FIG. 6 shows the curves of serum concentration over time; these were analyzed using the AUC function of Prism to determine the area under the curve (AUC), as reported in Table 10.

TABLE 10

Area-under-the-curve (AUC) of ADCs in mice

| Test item | AUC (µg*days/mL) Based on IgG detection | AUC (µg*days/mL) Based on toxin detection |
|---|---|---|
| hu4-2-17-PNU (adc828) | 460 ± 48 | 456 ± 48 |
| hu4-2-17-HC-PNU (adc822) | 730 ± 44 | 584 ± 42 |
| hu4-2-17-LC-PNU (adc826) | 1281 ± 119 | 1241 ± 126 |

The results of Table 10 lay forth a significantly higher exposure (AUC) of mice treated with ADC comprising the anthracycline payload at the light chain C-termini, than of mice treated with ADC comprising the anthracycline payload at both heavy and light chain C-termini, or the anthracycline payload at the heavy chain C-termini. Further, Table 10 lays forth that the ADC comprising the anthracycline payload at the heavy chain C-termini loses payload to a significant extent.

Example 8

Figure 7:
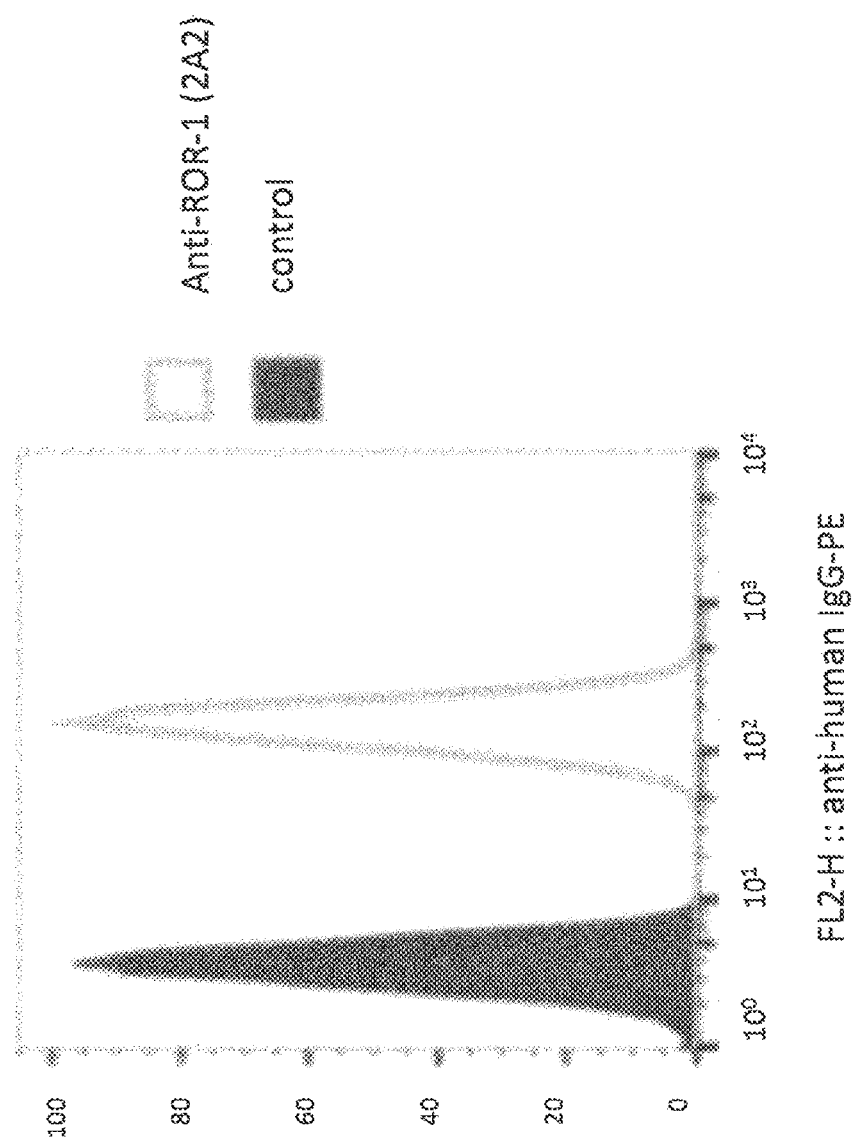
FIG. 7 shows the FACS analysis of expression of human ROR1 on engineered mouse EMT-6 breast cancer cells. EMT-6-ROR1 clone 14 selected for in vivo studies was analyzed by FACS staining for ROR1 expression with a fluorescently labeled anti-ROR1 antibody clone 2A2. The negative control shows staining of the same cells with a fluorescently labeled isotype-matched control antibody.

Murine EMT-6 breast cancer cells were cultured in DMEM complete (Dulbecco's Modified Eagle Medium (DMEM) High Glucose (4.5 g/L) with L-Glutamine with 10% (v/v) Fetal Calf Serum (FCS), 100 IU/mL of Pen-Strep-Fungizone and 2 mM L-glutamine (all Bioconcept, Allschwil, Switzerland)) at 37° C. and 5% $CO_2$. Cells were engineered to overexpress ROR1 by transposition as follows: cells were centrifuged (6 min, 1200 rpm, 4° C.) and resuspended in RPMI-1640 media ($5 \times 10^6$ cells/mL). 400 µL of cell suspension was added to 400 µL of RPMI containing 13.3 µg of transposable vector pPB-PGK-Puro-ROR1 (directing co-expression of full-length ROR1 (NP_005003.2) along with the puromycin-resistance gene) and 6.6 µg of transposase-containing vector pCDNA3.1_hy_mPB. DNA/EMT-6 cell mixture was transferred to electroporation cuvettes (0.4 cm-gap, 165-2088, BioRad, Cressier, Switzerland) and electroporated using the Biorad Gene Pulser II with capacitance extender at 300V and 950 µF. Then, cells were incubated for 5-10 min at room temperature. Following the incubation, cells were centrifuged at 1200 rpm for 6 min, washed once and subsequently resuspended in DMEM complete prior to incubation at 37° C. in a humidified incubator at 5% $CO_2$ atmosphere. One day after electroporation, cell pools stably expressing human ROR1 were selected by adding 3 µg/mL puromycin (Sigma-Aldrich, P8833). Single-cell clones expressing ROR1 were derived from antibiotic-selected EMT-6-ROR1 cells. Cells were then incubated with anti-ROR1 antibody 2A2 for 30 min (4° C., final concentration 2 µg/mL), followed by centrifugation and washing. Cells were then resuspended as previously and incubated with anti-human IgG antibody (Fc gamma-specific) PE (eBioscience, Vienna, Austria, 12-4998-82) with a 1:250 dilution in the dark (30 min, 4° C.), washed once in buffer and kept on ice until single-cell sorting of antigen-expressing cells by FACS using a FACSAriall instrument (BD Biocsiences, San Jose, USA). Expression of ROR1 on clone 14 used in the experiment below was determined by FACS (FIG. 7).

Example 9

Cytotoxicity of the CS1-targeting and ROR1-targeting ADCs of Table 11 was investigated using the ROR1-overexpressing EMT6 clone 14 cells of Example 8 and the CS1-positive L363 cell line. For this, the protocol of Example 4 was followed but plating 1000 EMT6 clone 14 and 10000 L363 cells per well in 754 DMEM supplemented with 10% by vol. FCS, 100 IU/mL Pen-Strep-Fungizone and 2 mM L-Glutamine at a density of $1.3 \times 10^4$ cells per well and $1.3 \times 10^5$ respectively.

TABLE 11

In vitro cell killing by ADCs (ng/mL)

| | Cell type | |
|---|---|---|
| ADC | ETM6 (clone 14) | L363 |
| ROR1 expression status | Positive | Negative |
| CS1 expression status | Negative | Positive |
| huERCS-409-LC-PNU (adc572), (G3-PNU) | 17.5 | 14'077 |
| huERCS-409-HC-PNU (adc758), (G3-PNU) | 14.4 | 5'316 |
| huERCS-409-LC-PNU (adc763), (G2-PNU) | 17.5 | 14'178 |
| huERCS-409-HC-PNU (adc762), (G2-PNU) | 16.7 | 7'959 |
| Hu4-2-17-LC-PNU (adc573), (G3-PNU) | Not converged | 10.3 |
| Hu4-2-17-HC-PNU (adc759), (G3-PNU) | Not converged | 16.4 |
| Hu4-2-17-LC-PNU (adc761), (G2-PNU) | Not converged | 18.2 |
| Hu4-2-17-HC-PNU (adc760), (G2-PNU) | Not converged | 23.1 |

Figure 8A:
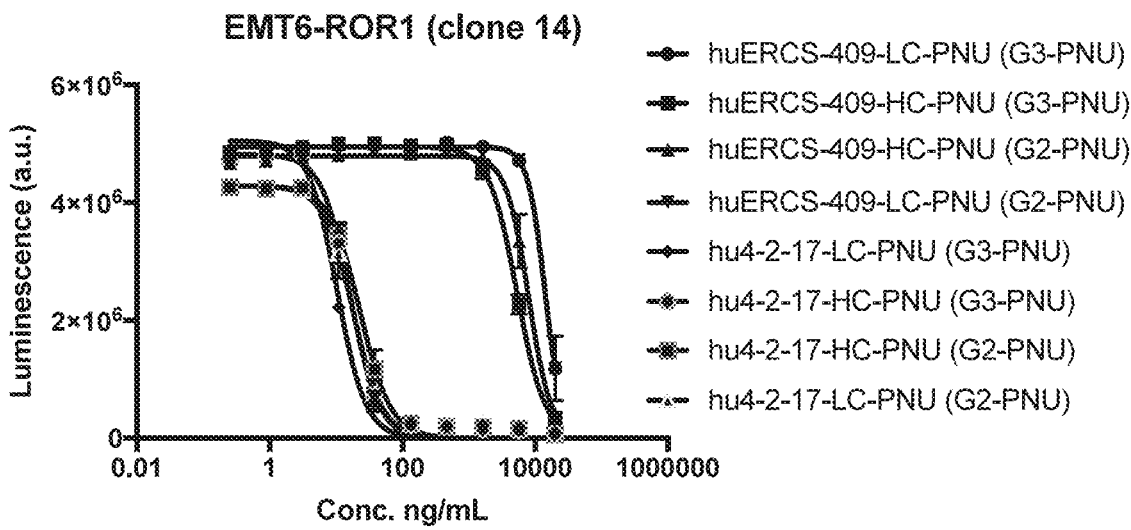
FIGS. 8A-8B show the dose-response curve of the in vitro cell killing assays on FIG. 8A the ROR1-overexpressing EMT6 clone 14 cells and FIG. 8B CS1-positive L363 (human plasma cell leukemia) cells with the following ADCs: huERCS-409-LC-PNU (a CS1-targeting ADC comprising G3-PNU linked to its light chain C-termini), huERCS-409-HC-PNU (a CS1-targeting ADC comprising G3-PNU linked to its heavy chain C-termini), huERCS-409-LC-PNU (a CS1-targeting ADC comprising G2-PNU linked to its light chain C-termini), huERCS-409-HC-PNU (a CS1-targeting ADC comprising G2-PNU linked to its heavy chain C-termini), hu4-2-17-LC-PNU (a ROR1-targeting ADC comprising G3-PNU linked to its light chain C-termini), hu4-2-17-HC-PNU (a ROR1-targeting ADC comprising G3-PNU linked to its heavy chain C-termini), hu4-2-17-LC-PNU (a ROR1-targeting ADC comprising G2-PNU linked to its light chain C-termini), and hu4-2-17-HC-PNU (a ROR1-targeting ADC comprising G2-PNU linked to its heavy chain C-termini). These results show that ADCs comprising anthracycline payloads exclusively on the heavy chain or exclusively on the light chain present comparable in vitro efficacy that is antigen-mediated.
Figure 8B:
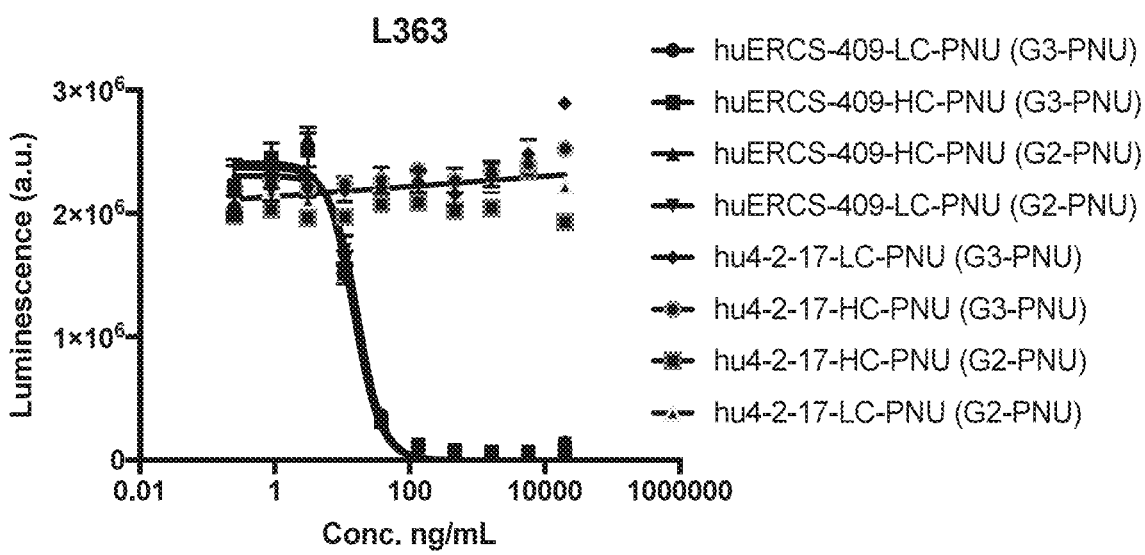

FIG. 8 shows the dose-response curve of the in vitro cell killing assays on the ROR1-overexpressing EMT6 clone 14 cells and L363 cells with the ADCs of Table 11. As per the Figure and Table, comparable ADCs comprising anthracycline payloads exclusively on the heavy chain or exclusively on the light chain present comparable in vitro efficacy that is antigen-mediated.

Example 10

The following study was conducted at ProQinase. On day 0, 1×10⁶ EMT-6-ROR1 clone 14 tumor cells (from Example 8) in 100 μl PBS were orthotopically implanted into the mammary fat pad of each 5-6-week old female BALB/c mouse. On reaching a mean tumor volume of approx. 30-80 mm³ (by caliper) on Day 3, mice were block-randomized into groups of 6 animals each according to tumour size. The ADCs of Table 12 (formulated in PBS) were administered on Day 3 at the indicated doses (by intravenous administration via bolus). Mice were provided water and pellets ad libitum. The evolution of tumor volume, (average per group and error bars corresponding to the standard error of the mean) evaluated twice-weekly by caliper, is presented in FIG. 9.

TABLE 12

ADC dosing in an orthotopic breast cancer model

| ADC | Dose (mg/kg) |
|---|---|
| Vehicle control (PBS) | — |
| Isotype control (Ac10-G3-PNU (adc517)) | 0.5 |
| hu4-2-17-PNU (adc519) | 0.5 |
| hu4-2-17-HC-PNU (adc520) | 1.0 |
| hu4-2-17-LC-PNU (adc521) | 1.0 |

Figure 9:
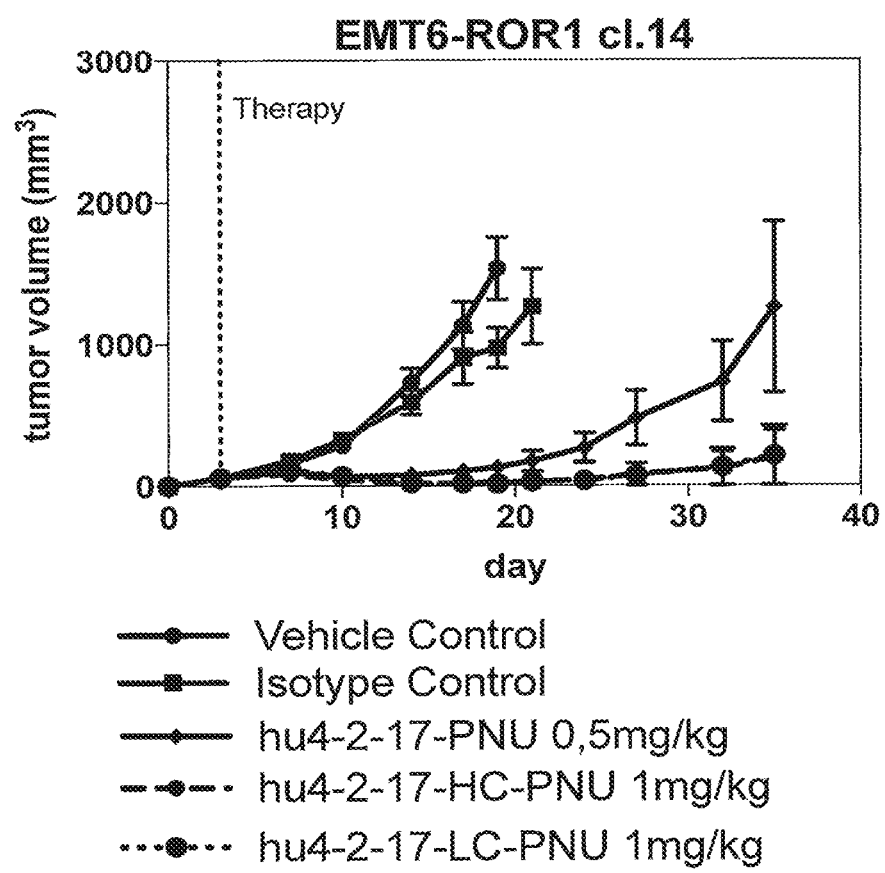
FIG. 9 shows evolution of ROR1-overexpressing EMT-6 (clone 14) tumor volume (by caliper; average per group with error bars corresponding to the standard error of the mean) of BALB/c female mice implanted orthotopically with tumor cells and treated with: vehicle control, 0.5 mg/kg of an isotype control ADC (a CD30-targeting ADC comprising an anthracycline molecule linked to both of its heavy chain C-termini); 0.5 mg/kg of hu4-2-17-PNU (a ROR1-targeting ADC with anthracycline payloads linked to both heavy and light chain C-termini), 1.0 mg/kg of hu4-2-17-HC-PNU (a ROR1-targeting ADC with anthracycline payloads linked to its heavy chain C-termini), and 1.0 mg/kg of hu4-2-17-LC-PNU (a ROR1-targeting ADC with anthracycline payloads on its light chain C-termini). At equal toxin load, the ROR1-targeting ADCs with toxins at only the heavy or only the light chain C-termini present superior in vivo efficacy relative to a ROR1-targeting ADCs with toxins both the heavy and light chain C-termini. ROR1-targeting ADCs with toxins at only the heavy or only the light chain C-termini present essentially equal in vivo efficacies.

The results of FIG. 9 lay forth that the ADCs of the invention comprising the anthracycline molecules at only the heavy chain C-termini or only at the light chain C-termini are essentially equally effective in vivo; their traces essentially entirely overlay.

As per the Examples presented herein, ADCs of the invention comprising the anthracycline molecules at the light chain C-termini are equal in terms of effectiveness on tumor cells and tumors relative to ADCs comprising anthracycline molecules at the heavy chain C-termini; however, ADCs of the invention comprising the anthracycline molecules at the light chain C-termini present remarkable advantageous properties in vivo including tolerability and stability.

REFERENCES

Beerli et al., "Sortase Enzyme-Mediated Generation of Site-Specifically Conjugated Antibody Drug Conjugates with High In Vitro and In Vivo Potency"; PloS One 10, e131177, 2015.

Chen et al., "A general strategy for the evolution of bond-forming enzymes using yeast display"; PNAS, 108(28), 2011.

Dorr et al., "Reprogramming the specificity of sortase enzymes"; PNAS, 2014.

Dorywalska et al., "Site-Dependent Degradation of a Non-Cleavable Auristatin-Based Linker-Payload in Rodent Plasma and its Effect on ADC Efficacy"; PLOS ONE, 2015.

Drake et al., "Aldehyde Tag Coupled with HIPS Chemistry Enables the Production of ADCs Conjugated Site-specifically to Different Antibody Regions with Distinct In vivo Efficacy and PK Outcomes"; Bioconjugate Chemistry, 25, 2014.

Jain et al., "Current ADC Linker Chemistry"; Pharma Res, 32, 2015.

Quintieri et al., "Formation and Antitumor Activity of PNU-159682, A Major Metabolite of Nemorubicin in Human Liver Microsomes"; Clin Cancer Res, 11, 2005.

Spirig et al., "Sortase enzymes in Gram-positive bacteria"; Molecular Microbiology, 82(5), 2011.

Strop et al., "Location Matters: Site of Conjugation Modulates Stability and Pharmacokinetics of Antibody Drug Conjugates"; Chemistry & Biology, 20, 2013.

Waldmeier et al., "Transpo-mAb display: Transposition-mediated B cell display and functional screening of full-length IgG antibody libraries"; mAbs, 8(4), 2016.

Swindells, et al., "abYsis: Integrated Antibody Sequence and Structure-Management, Analysis, and Prediction"; J. Mol. Biol. 429, 356-364, 2017

Sequences

The following sequences form part of the disclosure of the present application. A WIPO ST 25 compatible electronic sequence listing is provided with this application, too. For the avoidance of doubt, if discrepancies exist between the sequences in the following table and the electronic sequence listing, the sequences in this table shall be deemed to be the correct ones.

Amino Acid Sequence (with constant domain underlined, CDRs identified based on the Kabat system using abYsis software, Swindells et al., 2017, in bold) HC: heavy chain, LC: light chain

| NO. | Type | |
|---|---|---|
| 1 | Trastuzumab HC (K467R mutation) | EVQLVESGGGLVQPGGSLRLSCAASGFNIKDTYIHWVRQAPGKGLEWVARIYPTNG YTRYADSVKGRFTISADTSKNTAYLQMNSLRAEDTAVYYCSRWGGDGFYAMDYWGQ GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSISISP GR |
| 2 | Trastuzumab LC | DIQMTQSPSSLSASVGDRVTITCRASQDVNTAVAWYQQKPGKAPKLLIYSASFLYS GVPSRFSGSRSGTDFTLTISSLQPEDFATYYCQQHYTTPPTFGQGTKVEIKRTVAA PSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| 3 | Trastuzumab HC | EVQLVESGGGLVQPGGSLRLSCAASGFNIKDTYIHWVRQAPGKGLEWVARIYPTNG YTRYADSVKGRFTISADTSKNTAYLQMNSLRAEDTAVYYCSRWGGDGFYAMDYWGQ GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCD |

-continued

| NO. | Type | |
|---|---|---|
| | | KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPEN<br>NYKTTPPVLDSDGSFFLYSKLTVDKSRWQQGNVFSCSVMHEALHNHYTQKSISISP<br>GK |
| 4 | hu4-2-17 HC | QVQLRESGPGLVKPSETLSLTCTVSGFDISSYYMSWVRQPPGKGLEWIGAIGISGN<br>AYYASWAKSRVTISRDTSKNQFSLKLSSVTAADTAVYYCARDHPTYGMDLWGPGTL<br>VTVSSASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 5 | hu4-2-17 LC | SYELTQPPSVSVAPGKTARITCEGNNIGSKAVHWYQQKPGQAPVLVIYDDDERPSG<br>IPERFSGSNSGNTATLTISRVEAGDEADYYCQVWDSSAYVFGGGTKLTVLGQPKAA<br>PSVTLFPPSSEELQANKATLVCLISDFYPGAVTVAWKADSSPVKAGVETTTPSKQS<br>NNKYAASSYLSITPEQWKSHKSYSCQVTHEGSTVEKTVAPTECS |
| 6 | hu4-2-17 HC<br>(K467R<br>mutation) | QVQLRESGPGLVKPSETLSLTCTVSGFDISSYYMSWVRQPPGKGLEWIGAIGISGN<br>AYYASWAKSRVTISRDTSKNQFSLKLSSVTAADTAVYYCARDHPTYGMDLWGPGTL<br>VTVSSASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGR |
| 7 | huERCS-409<br>HC | EQQVVESGGGLVQPGGSLRLSCAVSGFSLNSYGVIWVRQAPGKGLEYVSIIGSSGN<br>TYYASSVKGRFTISRDTRLNTVYLQMNSLRAEDTAVYFCARYYGDSGFDSWGQGTL<br>VTVSSASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 8 | huERCS-409<br>LC | DQQLTQSPSSLSASVGDRVTITCRASQSIGSWLSWYQQKPGKAPKLLIYGASNLAS<br>GVPSRFSGSRSGTDYTLTISSLQPEDFATYYCLGASPNGWAFGQGTKVEIKRTVAA<br>PSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| 9 | huERCS-409<br>HC (K467R<br>mutation) | EQQVVESGGGLVQPGGSLRLSCAVSGFSLNSYGVIWVRQAPGKGLEYVSIIGSSGN<br>TYYASSVKGRFTISRDTRLNTVYLQMNSLRAEDTAVYFCARYYGDSGFDSWGQGTL<br>VTVSSASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGR |
| 10 | Ac10 HC | QIQLQQSGPEVVKPGASVKISCKASGYTFTDYYITWVKQKPGQGLEWIGWIYPGSG<br>NTKYNEKFKGKATLTVDTSSSTAFMQLSSLTSEDTAVYFCANYGNYWFAYWGQGTQ<br>VTVSAASTKGPSVFPLAPSSKSTSGGTAALGCLVKDYFPEPVTVSWNSGALTSGVH<br>TFPAVLQSSGLYSLSSVVTVPSSSLGTQTYICNVNHKPSNTKVDKKVEPKSCDKTH<br>TCPPCPAPELLGGPSVFLFPPKPKDTLMISRTPEVTCVVVDVSHEDPEVKFNWYVD<br>GVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSLSLSPGK |
| 11 | Ac10 LC | DIVLTQSPASLAVSLGQRATISCKASQSVDFDGDSYMNWYQQKPGQPPKVLIYAAS<br>NLESGIPARFSGSGSGTDFTLNIHPVEEEDAATYYCQQSNEDPWTFGGGTKLEIKR<br>TVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC |
| 12 | Sortase<br>recognition tag | LPXTG |
| 13 | Sortase<br>recognition tag | LPXAG |
| 14 | Sortase<br>recognition tag | LPXSG |
| 15 | Sortase<br>recognition tag | LAXTG |

| NO. | Type | |
|---|---|---|
| 16 | Sortase recognition tag | LPXTA |
| 17 | Sortase recognition tag | NPQTG |
| 18 | Sortase recognition tag | NPQTN |
| 19 | Sortase recognition tag | LPLTG |
| 20 | Sortase recognition tag | LAFTG |
| 21 | Sortase recognition tag | LPNTA |

What is claimed is:

1. An antibody drug conjugate (ADC) comprising:
an antibody, an antibody fragment or an antibody derivative retaining target binding properties, comprising at least one light chain constant region C-terminus, and an anthracycline-based small molecule,
wherein the anthracycline-based small molecule is exclusively linked to the light chain constant region C-terminus of the antibody, antibody fragment or antibody derivative retaining target binding properties, and
wherein the anthracycline-based small molecule is linked, via a linker comprising a peptidic sequence, to the antibody, antibody fragment or antibody derivative retaining target binding properties, and
wherein the anthracycline-based small molecule comprises the structure of formula (i)

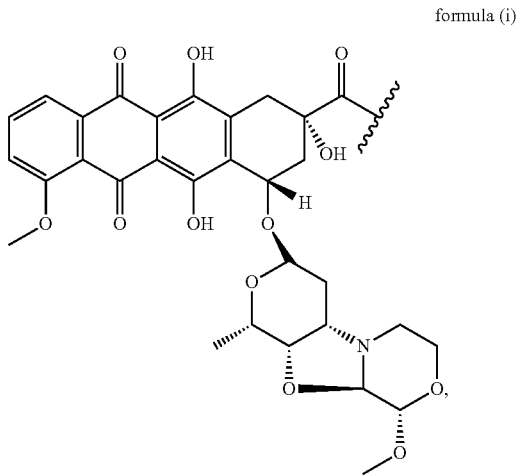

formula (i)

wherein the antibody drug conjugate comprises two light chain constant region C-termini and two anthracycline-based small molecules, and wherein the anthracycline-based small molecules are each exclusively linked to the light chain constant region C-termini of the antibody, antibody fragment, or antibody derivative.

2. The antibody drug conjugate according to claim 1, wherein the antibody, antibody fragment or antibody derivative retaining target binding properties binds to an antigen that is tumor specific or is expressed at a higher rate on tumor tissue than on healthy tissue.

3. The antibody drug conjugate according to claim 1, wherein the peptidic sequence of said linker comprises or consists of a peptidic motif resulting from specific cleavage of a sortase enzyme recognition motif.

4. The antibody drug conjugate according to claim 3, wherein said peptidic sequence of said linker comprises or consists of an oligoglycine sequence tag, denoted $G_n$ or $Gly_n$, where n is from 1 to 21.

5. The antibody drug conjugate according to claim 3, wherein the linker additionally comprises an alkyldiamino group of the form NH2-(CH2)$_m$-NH2, where m≥1 and ≤11.

6. The antibody drug conjugate according to claim 1, wherein the linker further comprises at least one further cleavable or non cleavable linker.

7. The antibody drug conjugate according to claim 1, which has a stoichiometric ratio between (i) antibody, antibody fragment, or antibody derivative and (ii) anthracycline-based small molecule of any value between 1 and 2.

8. A pharmaceutical composition comprising a therapeutically effective amount of the antibody drug conjugate according to claim 1, and a pharmaceutically acceptable carrier.

9. A method of producing an antibody drug conjugate according to claim 1,
which method comprises the following steps:
(a) providing an antibody, antibody fragment or antibody derivative retaining target binding properties, carrying a sortase enzyme recognition motif at the light chain C-terminus,
(b) providing one or more anthracycline-based small molecules each carrying an oligoglycine tag, and
(c) conjugating the antibody, antibody fragment or antibody derivative retaining target binding properties, and the one or more anthracycline-based small molecules by means of sortase-mediated conjugation using a sortase enzyme that recognizes said sortase enzyme recognition motif.

10. A method of treating a subject that is suffering from, at risk of developing, and/or diagnosed with a neoplastic disease, comprising administering to the subject a therapeutically effective amount of the antibody drug conjugate of claim 1.

11. The method of claim 10, wherein the neoplastic disease is breast cancer.

12. The antibody drug conjugate of claim 1, wherein the peptidic sequence of the linker comprises a spacer sequence.

13. The antibody drug conjugate of claim 12, wherein the spacer sequence is GGGGS (SEQ ID NO: 31).

14. The antibody drug conjugate of claim 12, wherein the peptidic sequence of the linker comprises GGGGSLPQTGG (SEQ ID NO: 32) following specific cleavage of a sortase enzyme recognition motif.

15. The antibody drug conjugate of claim 3, wherein the sortase enzyme recognition motif is selected from the group consisting of LPXTG (SEQ ID NO: 12), LPXAG (SEQ ID NO: 13), LPXSG (SEQ ID NO: 14), LAXTG (SEQ ID NO: 15), LPXTA (SEQ ID NO: 16), NPQTG (SEQ ID NO: 17), NPQTN (SEQ ID NO: 18), LPLTG (SEQ ID NO: 19), LAFTG (SEQ ID NO: 20) and LPNTA (SEQ ID NO: 21), where X is any amino acid.

16. The antibody drug conjugate of claim 3, wherein the sortase enzyme recognition motif is LPQTG (SEQ ID NO:30).

17. The antibody drug conjugate of claim 4, wherein n is 2.

18. The antibody drug conjugate of claim 5, wherein m is 2.

19. The antibody drug conjugate of claim 6, wherein the at least one further cleavable or non-cleavable linker is selected from the group consisting of: a hydrazine linker, a thiourea linker, a self-immolative linker, a succinimidyl trans-4-(maleimidylmethyl)cyclohexane-1-carboxylate (SMCC) linker, a disulfide linker, a selenoether linker, an amide linker, a thioether linker, and a maleimide linker.

* * * * *

SEQUENCE LISTING

<160> NUMBER OF SEQ ID NOS: 32

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Trastuzumab HC (K467R mutation)

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Arg
    450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Trastuzumab LC

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Trastuzumab HC

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220
```

-continued

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 4
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu4-2-17 HC

<400> SEQUENCE: 4

Gln Val Gln Leu Arg Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Asp His Pro Thr Tyr Gly Met Asp Leu Trp Gly Pro Gly Thr Leu
        100                 105                 110
```

```
Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 5
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu4-2-17 LC

<400> SEQUENCE: 5

Ser Tyr Glu Leu Thr Gln Pro Pro Ser Val Ser Val Ala Pro Gly Lys
1               5                   10                  15
```

```
Thr Ala Arg Ile Thr Cys Glu Gly Asn Asn Ile Gly Ser Lys Ala Val
            20                  25                  30

His Trp Tyr Gln Gln Lys Pro Gly Gln Ala Pro Val Leu Val Ile Tyr
        35                  40                  45

Asp Asp Asp Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Lys Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 6
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu4-2-17 HC (K467R mutation)

<400> SEQUENCE: 6

Gln Val Gln Leu Arg Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Arg
        435                 440                 445

<210> SEQ ID NO 7
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huERCS-409 HC

<400> SEQUENCE: 7

Glu Gln Gln Val Val Glu Ser Gly Gly Gly Leu Val Gln Pro Gly Gly
1               5                   10                  15

Ser Leu Arg Leu Ser Cys Ala Val Ser Gly Phe Ser Leu Asn Ser Tyr
            20                  25                  30

Gly Val Ile Trp Val Arg Gln Ala Pro Gly Lys Gly Leu Glu Tyr Val
        35                  40                  45
```

```
Ser Ile Ile Gly Ser Ser Gly Asn Thr Tyr Tyr Ala Ser Ser Val Lys
 50                  55                  60

Gly Arg Phe Thr Ile Ser Arg Asp Thr Arg Leu Asn Thr Val Tyr Leu
 65                  70                  75                  80

Gln Met Asn Ser Leu Arg Ala Glu Asp Thr Ala Val Tyr Phe Cys Ala
                 85                  90                  95

Arg Tyr Tyr Gly Asp Ser Gly Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 8
<211> LENGTH: 214
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huERCS-409 LC

<400> SEQUENCE: 8

Asp Gln Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ser Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
    50                  55                  60

Ser Arg Ser Gly Thr Asp Tyr Thr Leu Thr Ile Ser Ser Leu Gln Pro
65                  70                  75                  80

Glu Asp Phe Ala Thr Tyr Tyr Cys Leu Gly Ala Ser Pro Asn Gly Trp
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huERCS-409 HC (K467R mutation)

<400> SEQUENCE: 9

Glu Gln Gln Val Val Glu Ser Gly Gly Gly Leu Val Gln Pro Gly Gly
1               5                   10                  15

Ser Leu Arg Leu Ser Cys Ala Val Ser Gly Phe Ser Leu Asn Ser Tyr
            20                  25                  30

Gly Val Ile Trp Val Arg Gln Ala Pro Gly Lys Gly Leu Glu Tyr Val
        35                  40                  45

Ser Ile Ile Gly Ser Ser Gly Asn Thr Tyr Tyr Ala Ser Ser Val Lys
    50                  55                  60

Gly Arg Phe Thr Ile Ser Arg Asp Thr Arg Leu Asn Thr Val Tyr Leu
65                  70                  75                  80
```

Gln Met Asn Ser Leu Arg Ala Glu Asp Thr Ala Val Tyr Phe Cys Ala
            85                  90                  95

Arg Tyr Tyr Gly Asp Ser Gly Phe Asp Ser Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Arg
            435                 440                 445

<210> SEQ ID NO 10
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Ac10 HC

<400> SEQUENCE: 10

```
Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
        435                 440                 445

<210> SEQ ID NO 11
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Ac10 LC

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag
<220> FEATURE:
<221> NAME/KEY: MOD_RES
<222> LOCATION: (3)..(3)
<223> OTHER INFORMATION: Any amino acid
```

```
<400> SEQUENCE: 12

Leu Pro Xaa Thr Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag
<220> FEATURE:
<221> NAME/KEY: MOD_RES
<222> LOCATION: (3)..(3)
<223> OTHER INFORMATION: Any amino acid

<400> SEQUENCE: 13

Leu Pro Xaa Ala Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag
<220> FEATURE:
<221> NAME/KEY: MOD_RES
<222> LOCATION: (3)..(3)
<223> OTHER INFORMATION: Any amino acid

<400> SEQUENCE: 14

Leu Pro Xaa Ser Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag
<220> FEATURE:
<221> NAME/KEY: MOD_RES
<222> LOCATION: (3)..(3)
<223> OTHER INFORMATION: Any amino acid

<400> SEQUENCE: 15

Leu Ala Xaa Thr Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag
<220> FEATURE:
<221> NAME/KEY: MOD_RES
<222> LOCATION: (3)..(3)
<223> OTHER INFORMATION: Any amino acid
```

```
<400> SEQUENCE: 16

Leu Pro Xaa Thr Ala
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag

<400> SEQUENCE: 17

Asn Pro Gln Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag

<400> SEQUENCE: 18

Asn Pro Gln Thr Asn
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag

<400> SEQUENCE: 19

Leu Pro Leu Thr Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sortase recognition tag

<400> SEQUENCE: 20

Leu Ala Phe Thr Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: Sortase recognition tag

<400> SEQUENCE: 21

Leu Pro Asn Thr Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hu4-2-17 HCDR1

<400> SEQUENCE: 22

Ser Tyr Met Met Ser
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hu4-2-17 HCDR2

<400> SEQUENCE: 23

Ala Ile Gly Ile Ser Gly Asn Ala Tyr Tyr Ala Ser Trp Ala Lys Ser
1               5                   10                  15

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hu4-2-17 HCDR3

<400> SEQUENCE: 24

Asp His Pro Thr Tyr Gly Met Asp Leu
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hu4-2-17 LCDR1

<400> SEQUENCE: 25

Glu Gly Asn Asn Ile Gly Ser Lys Ala Val His
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<223> OTHER INFORMATION: hu4-2-17 LCDR2

<400> SEQUENCE: 26

Asp Asp Asp Glu Arg Pro Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: hu4-2-17 LCDR3

<400> SEQUENCE: 27

Gln Val Trp Asp Ser Ser Ala Tyr Val
1               5

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu4-2-17 VH

<400> SEQUENCE: 28

Gln Val Gln Leu Arg Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: hu4-2-17 VL

<400> SEQUENCE: 29

Ser Tyr Glu Leu Thr Gln Pro Pro Ser Val Ser Val Ala Pro Gly Lys
1               5                   10                  15

Thr Ala Arg Ile Thr Cys Glu Gly Asn Asn Ile Gly Ser Lys Ala Val
            20                  25                  30
```

His Trp Tyr Gln Gln Lys Pro Gly Gln Ala Pro Val Leu Val Ile Tyr
            35                  40                  45

Asp Asp Asp Glu Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu
            100                 105

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptidic motif resulting from specific cleavage
      of sortase enzyme recognition site

<400> SEQUENCE: 30

Leu Pro Gln Thr
1

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Spacer

<400> SEQUENCE: 31

Gly Gly Gly Gly Ser
1               5

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 32

Gly Gly Gly Gly Ser Leu Pro Gln Thr Gly Gly
1               5                   10